US012303609B1

(12) United States Patent
Hsu et al.

(10) Patent No.: US 12,303,609 B1
(45) Date of Patent: May 20, 2025

(54) AQUA-OZONE HYGIENIZATION

(71) Applicant: Biotek Environmental Science Ltd, New Taipei (TW)

(72) Inventors: Gavin Hsu, Taipei (TW); Maxwell Hsu, New Taipei (TW); Darren Simmons, Fair Oaks Ranch, TX (US); Ivor J. J. Longo, Atlanta, TX (US); H. Brock Kolls, Alpharetta, GA (US)

(73) Assignee: Biotek Environmental Science Ltd, New Taipei (TW)

( * ) Notice: Subject to any disclaimer, the term of this patent is extended or adjusted under 35 U.S.C. 154(b) by 0 days.

(21) Appl. No.: 18/888,218

(22) Filed: Sep. 18, 2024

Related U.S. Application Data

(63) Continuation-in-part of application No. 18/782,055, filed on Jul. 24, 2024, and a continuation-in-part of
(Continued)

(51) Int. Cl.
*A61L 2/18* (2006.01)
*A61L 2/22* (2006.01)
(Continued)

(52) U.S. Cl.
CPC ............... *A61L 2/183* (2013.01); *A61L 2/22* (2013.01); *A61L 2/24* (2013.01); *A61L 2/26* (2013.01); *C02F 1/46104* (2013.01); *D06F 34/04* (2020.02); *D06F 34/22* (2020.02); *D06F 35/001* (2013.01); *D06F 39/087* (2013.01); *D06F 39/088* (2013.01); *A61L 2202/11* (2013.01); *A61L 2202/122* (2013.01); *A61L 2202/14* (2013.01); *A61L 2202/15* (2013.01);
(Continued)

(58) Field of Classification Search
CPC ... A61L 2/183; A61L 2/22; A61L 2/24; A61L 2/26; D06F 34/22; D06F 34/04; D06F 35/001; D06F 39/087; D06F 39/088
See application file for complete search history.

(56) References Cited

U.S. PATENT DOCUMENTS

2005/0147527 A1* 7/2005 Brown ................... A61L 2/208
422/292

FOREIGN PATENT DOCUMENTS

CN 210750400 U * 6/2020

OTHER PUBLICATIONS

English Translation of CN210750400 (Year: 2020).*

* cited by examiner

*Primary Examiner* — Sean E Conley
(74) *Attorney, Agent, or Firm* — H. Brock Kolls

(57) ABSTRACT

An aqua-ozone hygienization system is disclosed, including a tank configured to hold an item for treatment. The system enables user selection between three hygienization methods: a non-wetting atomized mist for deodorization, a wetting spray for disinfection, or an immersion for comprehensive purification, deodorization, and disinfection. A platform within the tank forms a water reservoir beneath it and provides a top surface for item placement. The system includes an electrochemical generator that produces ozonated concentrate liquid from water, supplied by a circulating pump drawing from the reservoir. A nozzle connected to the electrochemical generator is switchable between dispensing the ozonated concentrate liquid as either an atomized mist or spray. During operation, the liquid is either misted or sprayed onto the item, or accumulates on the platform to immerse the item, depending on the selected treatment method.

22 Claims, 14 Drawing Sheets

Related U.S. Application Data application No. 18/782,058, filed on Jul. 24, 2024, now Pat. No. 12,194,164, and a continuation-in-part of application No. 18/760,274, filed on Jul. 1, 2024, now Pat. No. 12,151,055, and a continuation-in-part of application No. 18/760,262, filed on Jul. 1, 2024, now Pat. No. 12,171,914, and a continuation-in-part of application No. 18/646,394, filed on Apr. 25, 2024, and a continuation-in-part of application No. 18/628,680, filed on Apr. 6, 2024, now Pat. No. 12,137,699.

(51) Int. Cl.
*A61L 2/24* (2006.01)
*A61L 2/26* (2006.01)
*C02F 1/461* (2023.01)
*D06F 34/04* (2020.01)
*D06F 34/22* (2020.01)
*D06F 35/00* (2006.01)
*D06F 39/08* (2006.01)
*D06F 103/18* (2020.01)
*D06F 103/20* (2020.01)
*D06F 105/02* (2020.01)
*D06F 105/08* (2020.01)
*D06F 105/58* (2020.01)

(52) U.S. Cl.
CPC ....... *A61L 2202/17* (2013.01); *A61L 2202/26* (2013.01); *C02F 2201/4611* (2013.01); *C02F 2201/4612* (2013.01); *C02F 2209/23* (2013.01); *C02F 2209/42* (2013.01); *D06F 2103/18* (2020.02); *D06F 2103/20* (2020.02); *D06F 2105/02* (2020.02); *D06F 2105/08* (2020.02); *D06F 2105/58* (2020.02)

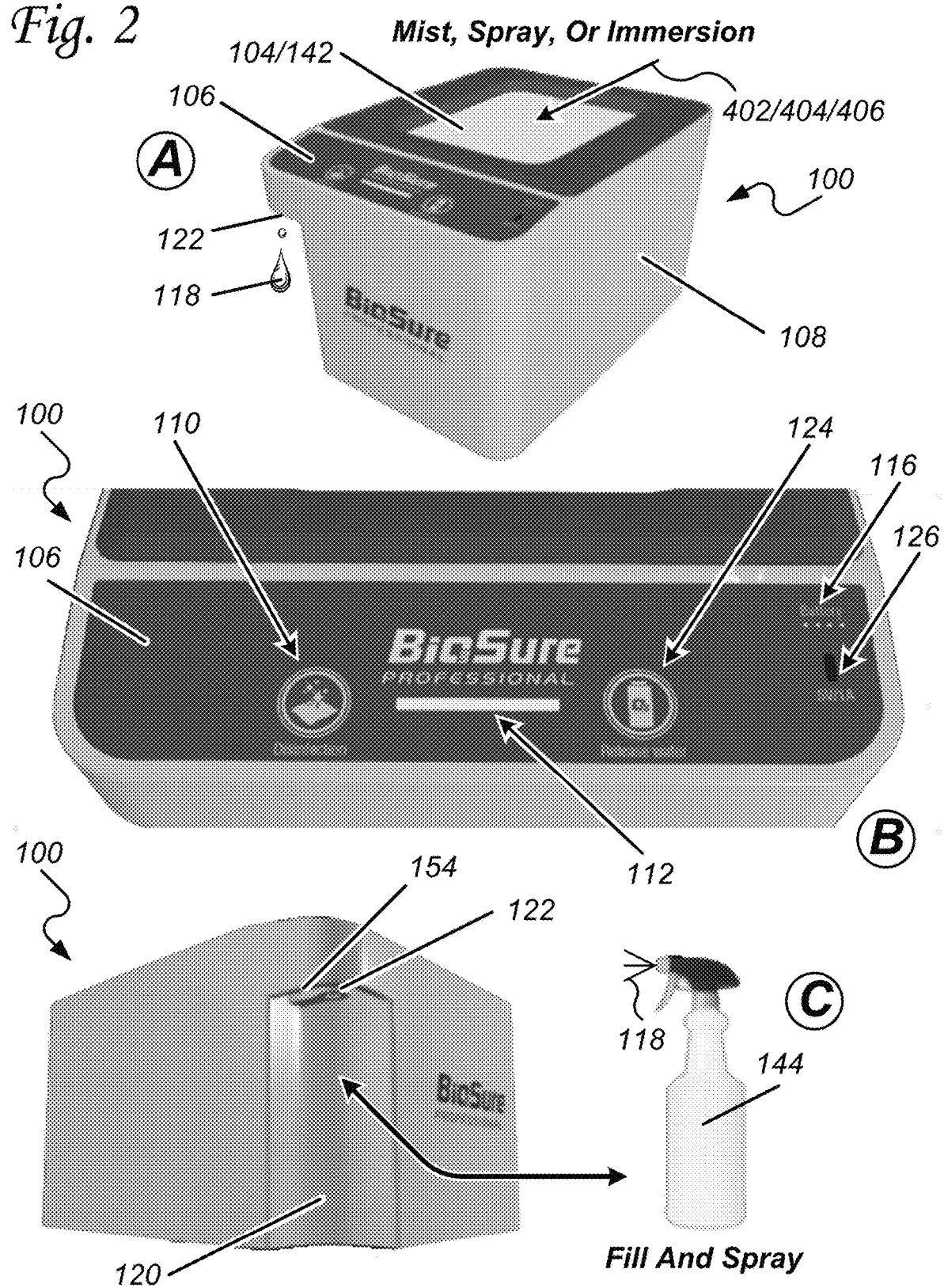

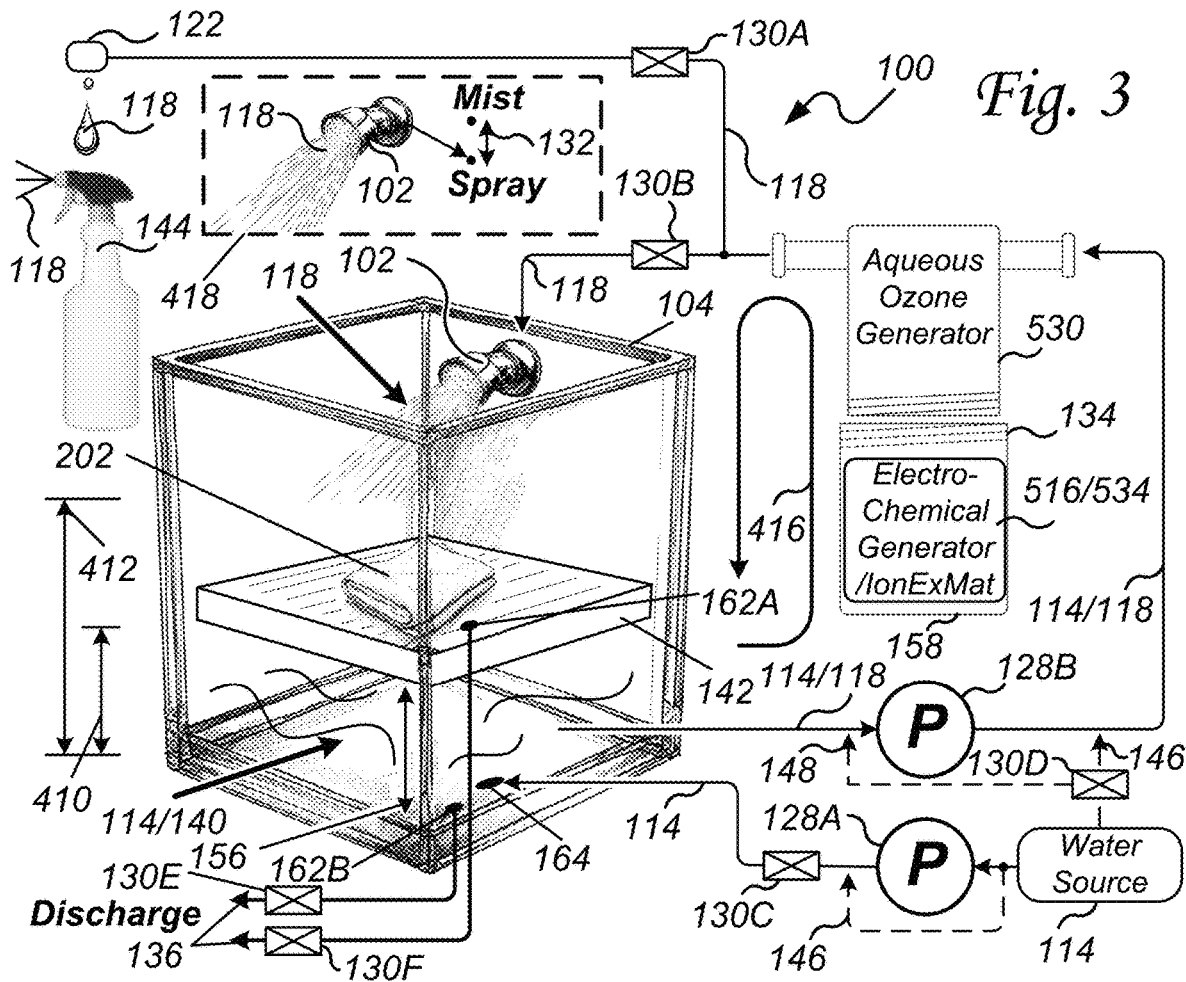
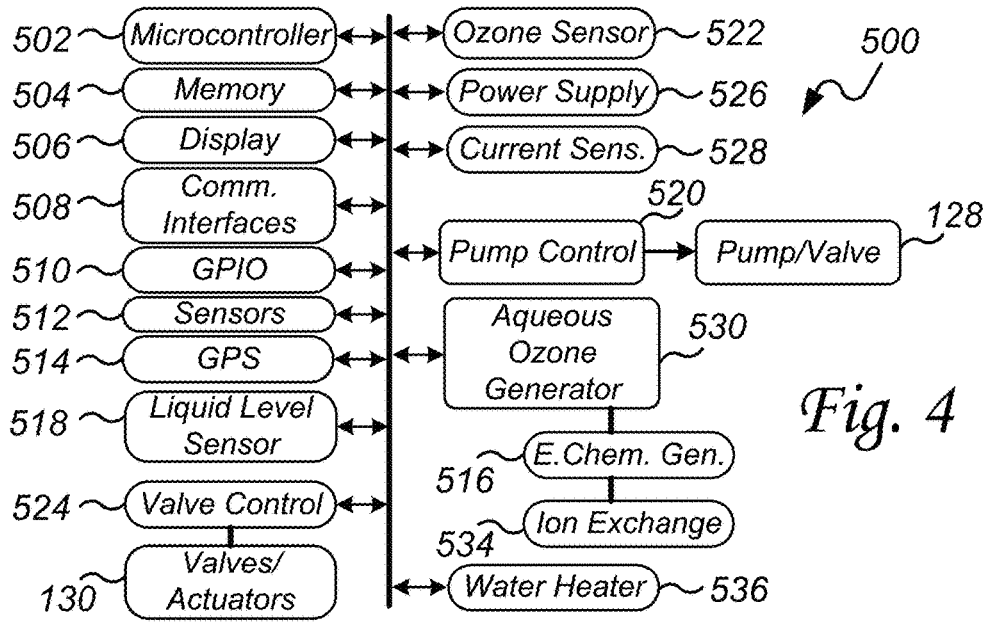

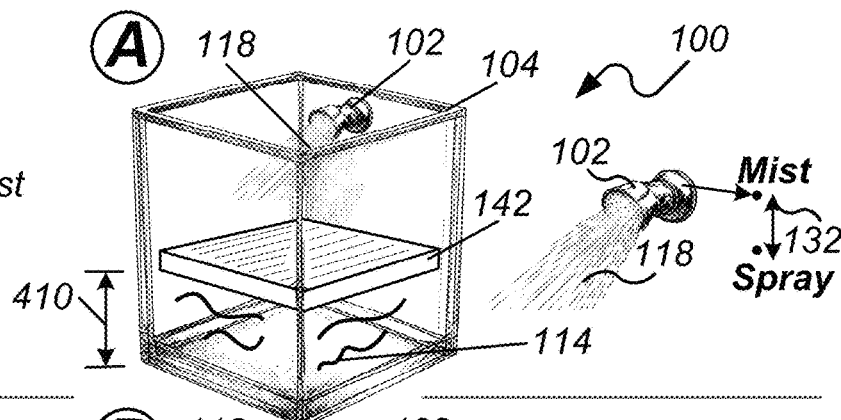
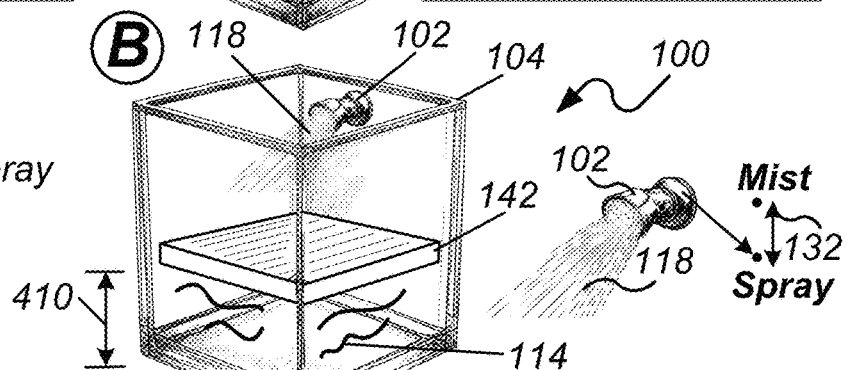
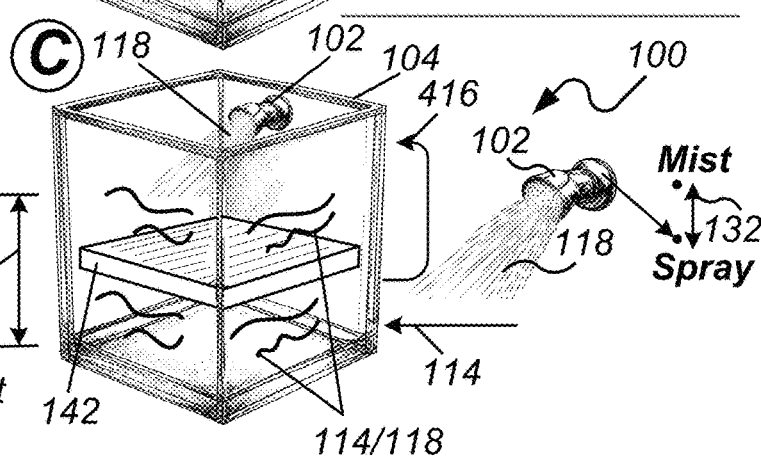
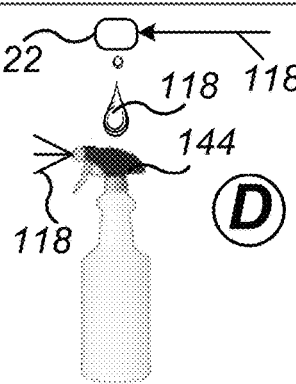
Fig. 5

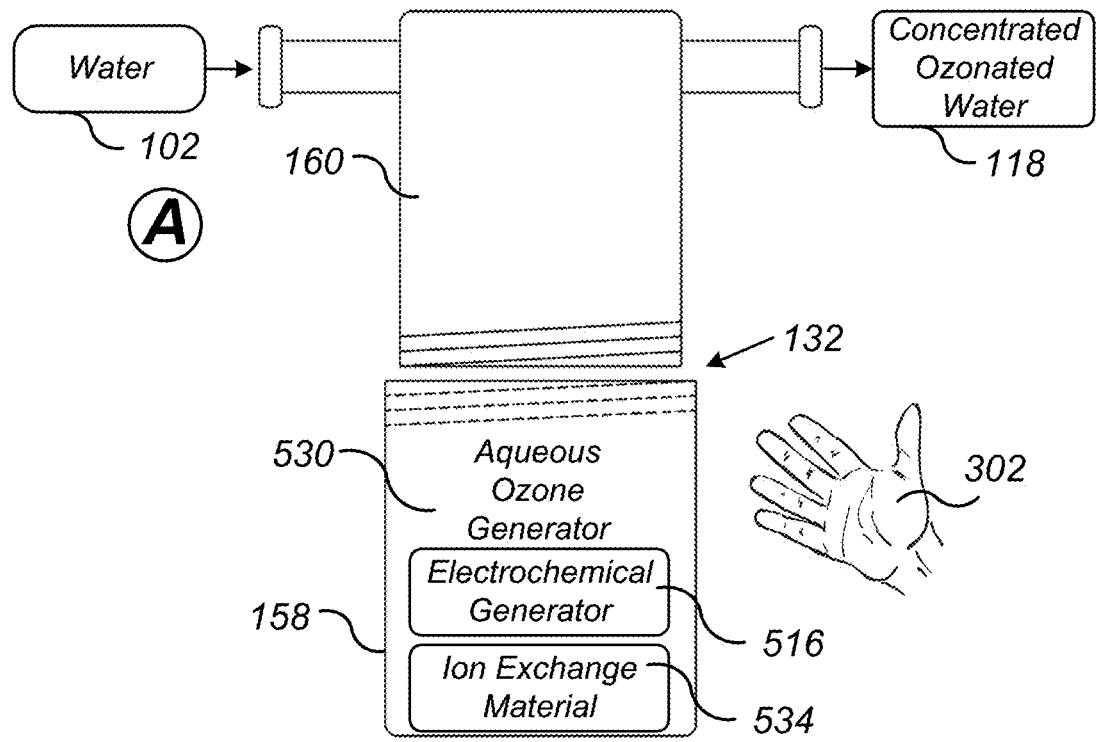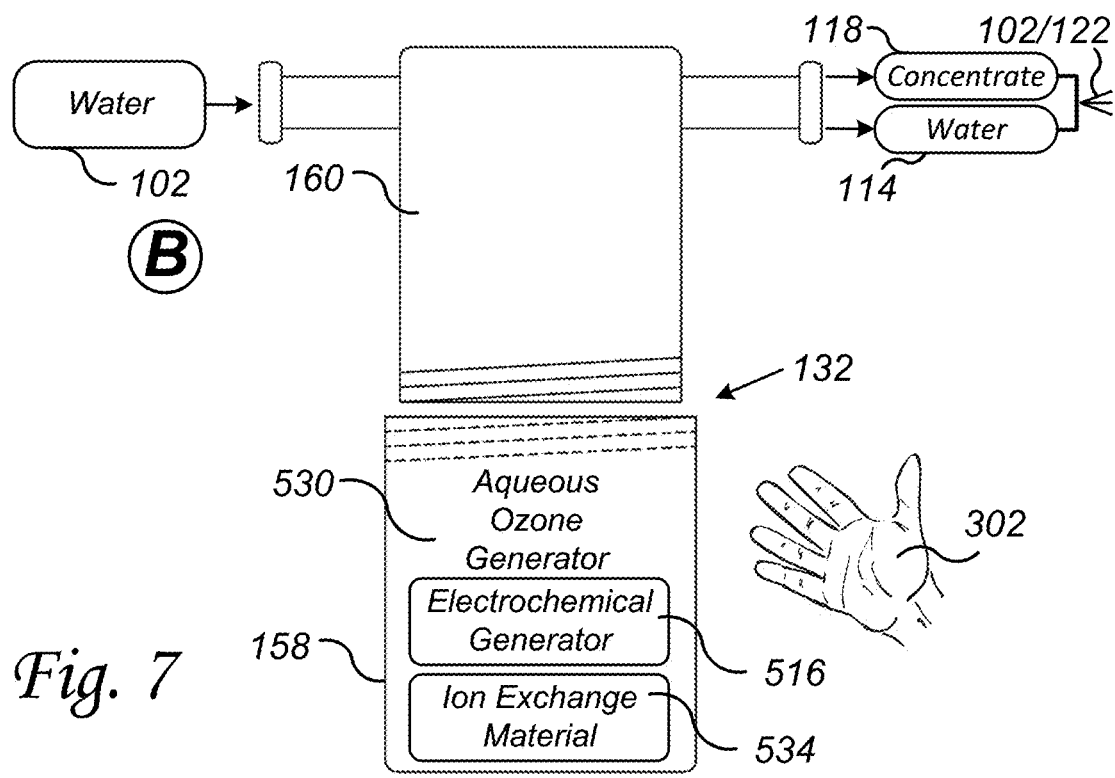
Fig. 7

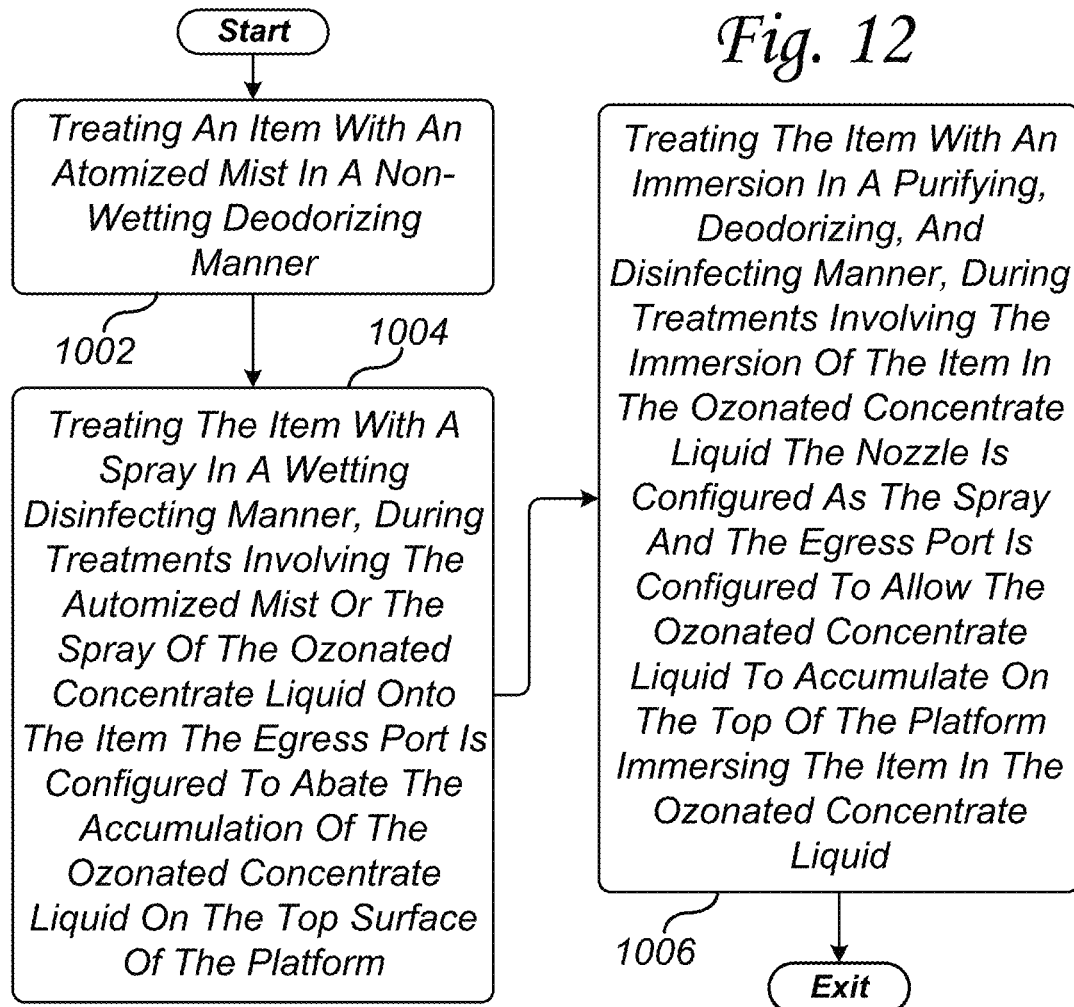
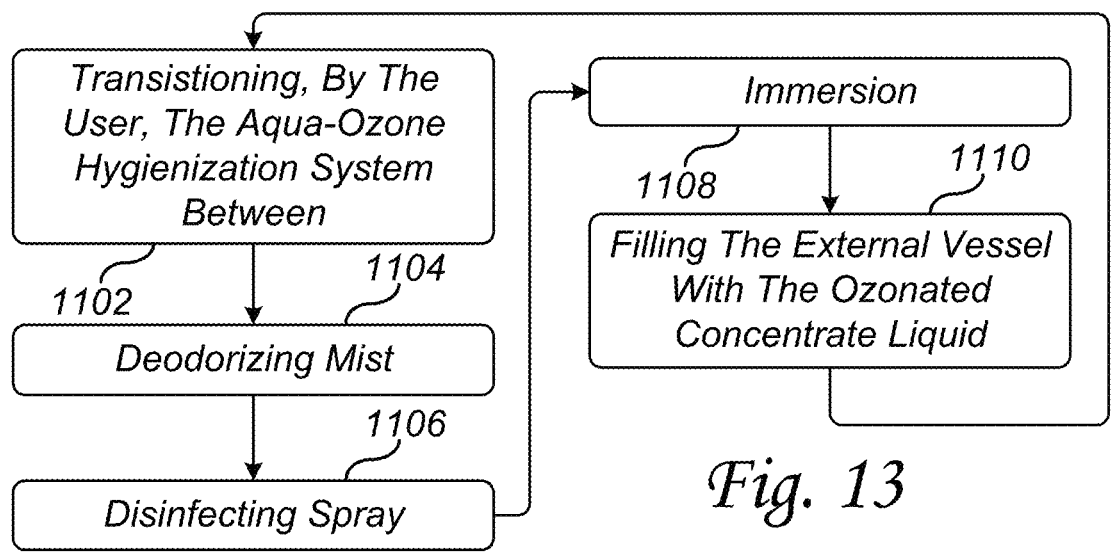

AQUA-OZONE HYGIENIZATION

CROSS-REFERENCE TO RELATED TREATMENTS

This application contains subject matter which is related to the subject matter of the following application. The below-listed applications are hereby incorporated herein by reference in their entirety:

This U.S. non-provisional application is a continuation in part of a U.S. non-provisional application Ser. No. 18/782,055, inventor Darren Simmons et al., entitled "MICROFOAMING AQUEOUS OZONE DISINFECTION", filed Jul. 24, 2024; and is a continuation in part of U.S. non-provisional application Ser. No. 18/782,058, inventor Darren Simmons et al., entitled "MICROFOAMING AQUEOUS OZONE DISINFECTION", filed Jul. 24, 2024;

This U.S. non-provisional application is a continuation in part of a U.S. non-provisional application Ser. No. 18/760,262, inventor Gavin Hsu et al., entitled "DEODORIZING AIR USING AQUEOUS OZONE AS A CATALYST", filed Jul. 1, 2024; and is a continuation in part of U.S. non-provisional application Ser. No. 18/760,274, inventor Gavin Hsu et al., entitled "DEODORIZING AIR USING AQUEOUS OZONE AS A CATALYST", filed Jul. 1, 2024;

This U.S. non-provisional application is a continuation in part of a U.S. non-provisional application Ser. No. 18/628,680, inventor Darren Simmons et al., entitled "FOOD PREPARATION DISINFECTION TREATMENT METHODS", filed Apr. 6, 2024; which is a continuation in part of U.S. non-provisional application Ser. No. 18/428,523, inventor Darren Simmons et al., entitled "AQUEOUS OZONE DISINFECTION SYSTEM", filed Jan. 31, 2024, now U.S. Pat. No. 12,070,051; and This U.S. non-provisional application is a continuation in part of a U.S. non-provisional application Ser. No. 18/646,394, inventor Darren Simmons et al., entitled "AQUEOUS OZONE FLOOR DISINFECTION SYSTEM", filed Apr. 25, 2024; which is a continuation in part of U.S. non-provisional application Ser. No. 18/528,194, inventor Darren Simmons et al., entitled "AQUEOUS OZONE FLOOR DISINFECTION SYSTEM", filed Dec. 4, 2023, now U.S. Pat. No. 12,036,331; and a continuation in part of U.S. non-provisional application Ser. No. 18/528,162, inventor Darren Simmons et al., entitled "AQUEOUS OZONE FLOOR DISINFECTION SYSTEM", filed Dec. 4, 2023, now U.S. Pat. No. 11,975,118.

TECHNICAL FIELD OF THE INVENTION

The present invention relates to an aqua-ozone hygienization system designed for versatile and efficient treatment of various items such as towels, clothing, and other suitable items. The system is housed within a tank that holds the item to be treated. Central to its operation is the ability to select between three distinct hygienization methods: (1) a non-wetting atomized mist, which provides deodorization by dispersing a fine layer of ozonated concentrate liquid over the item; (2) a wetting spray, which delivers a more substantial layer of the same ozonated concentrate for effective disinfection; and (3) an immersion method, wherein the item is fully submerged in the ozonated concentrate liquid, achieving thorough purification, deodorization, and disinfection.

The system features a platform within the tank, which forms a water reservoir underneath it. The platform's top surface supports the item during treatment. Water from the reservoir is circulated by a pump to an electrochemical generator, where it is converted into an ozonated concentrate liquid. This ozonated concentrate liquid is then directed to a nozzle, which can be adjusted to dispense the liquid as either an atomized mist or a spray. The selected application method determines whether the liquid remains on the item's surface or accumulates on the platform, resulting in immersion. The system is designed to offer flexible and comprehensive hygienization options, making it adaptable to various needs and applications.

BACKGROUND OF THE INVENTION

Before our invention, washing systems face several significant shortcomings that limit their public use effectiveness, safety, and convenience, particularly in modern, fast-paced environments. One shortcoming is the use of ozone generation by way of corona discharge in many conventional wash systems. While this method produces ozone for use, it also inadvertently generates harmful nitrogen species compounds as byproducts. These nitrogen species compounds, when inhaled, can pose serious health risks, including respiratory issues and other adverse effects. As a result, corona discharge-generated ozone systems are unsafe for use in environments where humans may be exposed to the ozone gas (and undesirable nitrogen species), such as in wash areas or laundries, where users could come into contact with or breathe the gas. This safety concern significantly restricts the practical application of such systems in everyday environments and in particular in public environments.

Another shortcoming of prior wash systems, such as those resembling kitchen sinks, is their reliance on soaking items in water. While soaking is effective for thorough cleaning, it completely wets the clothing or textile items, requiring a drying phase before the items can be used or worn again. This process is particularly inconvenient when users need the items to be immediately usable after washing, as is often the case in time-sensitive situations or on-the-go scenarios.

Furthermore, existing wash systems are generally not designed to meet the needs of users in fast-paced, on-the-go environments like fitness centers, gyms, or other active venues. In these settings, users often need to quickly freshen up textile items such as towels and workout clothes before use, thoroughly clean them after use, and freshen up items like shirts or blouses to be worn immediately after a workout without residual odors like gym smells, sweat, or cigarette smoke. Traditional wash systems do not offer the flexibility to accommodate these varied needs, particularly in a way that allows for immediate use of the items without a drying period. This lack of adaptability makes them ill-suited for modern lifestyle demands, where efficiency, safety, and convenience are essential.

The present invention addresses these and other shortcomings by providing a new solution and treatment methods that are safe, effective, and adaptable to a wide range of environments. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of an aqua-ozone hygienization system comprising a tank configured to hold an item for hygienization. Hygienization is effectuated by way of a user selecting between treating the item with an atomized mist in a non-wetting deodorizing manner, a spray in a wetting disinfecting manner, or an immersion in a purifying, deodorizing, and disinfecting manner.

A platform is positioned within the tank, the platform forms a water reservoir located beneath the platform. The platform has a top surface for placing the item to be treated. An electrochemical generator is configured to generate an ozonated concentrate liquid from water. A circulating pump is configured to draw water from the water reservoir and supply the water to the electrochemical generator. A nozzle is in fluid communication with the electrochemical generator. The nozzle is switchable between dispensing the ozonated concentrate liquid onto the item as the atomized mist or as the spray. And, an egress port is configured to drain the ozonated concentrate liquid from the top surface of the platform.

In operation, during treatments involving the atomized mist or the spray of the ozonated concentrate liquid onto the item the egress port is configured to abate accumulation of the ozonated concentrate liquid on the top surface of the platform. And, during treatments involving the immersion of the item in the ozonated concentrate liquid, the nozzle is configured as the spray and the egress port is configured to allow the ozonated concentrate liquid to accumulate on the top of the platform immersing the item in the ozonated concentrate liquid, upon completion of the immersion. The egress port is configured to discharge the ozonated concentrate liquid from the top surface of the platform.

Additional shortcomings of the prior art are overcome and additional advantages are provided through the provision of an aqua-ozone hygienization system comprising a tank configured to hold an item for hygienization, hygienization is effectuated by way of a user selecting between treating the item with an atomized mist in a non-wetting deodorizing manner, a spray in a wetting disinfecting manner, or an immersion in a purifying, deodorizing, and disinfecting manner.

A platform is positioned within the tank. The platform forms a water reservoir located beneath the platform. The platform has a top surface for placing the item to be treated. An electrochemical generator is configured to generate an ozonated concentrate liquid from water. A circulating pump is configured to draw water from the water reservoir and supply the water to the electrochemical generator. A nozzle is in fluid communication with the electrochemical generator. The nozzle is switchable between dispensing the ozonated concentrate liquid onto the item as the atomized mist or as the spray. An ingress port is configured to allow water to fill the water reservoir.

In operation, during treatments involving the atomized mist or the spray of the ozonated concentrate liquid onto the item the ozonated concentrate liquid is absent accumulation on the top surface of the platform. And, during treatments involving the immersion of the item, water is added by way of the ingress port to the water reservoir, raising the water level to an immersion level above the platform, immersing the item on the platform. The circulating pump and the electrochemical generator are operated to produce and dispense, by way of the nozzle, the ozonated concentrate liquid into the tank mixing with the water creating a mixture until a desired ozone concentration of the mixture is achieved.

Additional shortcomings of the prior art are overcome and additional advantages are provided through the provision of an aqua-ozone hygienization system comprising a tank configured to hold an item for hygienization. Hygienization is effectuated by way of a user selecting between treating the item with an atomized mist in a non-wetting deodorizing manner, a spray in a wetting disinfecting manner, or an immersion in a purifying, deodorizing, and disinfecting manner.

A platform is positioned within the tank, the platform in an extended position forms a water reservoir which comprises water located beneath the platform and in a retracted position is immersed into the water reservoir. The platform has a top surface for placing the item to be treated. An electrochemical generator is configured to generate an ozonated concentrate liquid from water. A circulating pump is configured to draw water from the water reservoir and supply the water to the electrochemical generator. And, a nozzle is in fluid communication with the electrochemical generator, the nozzle is switchable between dispensing the ozonated concentrate liquid onto the item as the atomized mist or as the spray.

In operation, during treatments involving the atomized mist or the spray of the ozonated concentrate liquid onto the item the platform is in the extended position and the ozonated concentrate liquid is absent accumulation on the top surface of the platform. During treatments involving the immersion of the item, the platform is in the retracted position lowering the item into and immersing the item in the water reservoir, the circulating pump and the electrochemical generator are operated to produce and dispense, by way of the nozzle, the ozonated concentrate liquid into the tank mixing with the water creating a mixture until a desired ozone concentration of the mixture is achieved.

Additional shortcomings of the prior art are overcome and additional advantages are provided through the provision of a method of transitioning an aqua-ozone hygienization system between a deodorizing atomized mist, a disinfection spray, and a purifying, deodorizing, and disinfecting immersion. The method comprises the steps of treating an item with an atomized mist on an ozonated concentrate liquid, in a non-wetting deodorizing manner.

The aqua-ozone hygienization system comprises a tank, and a platform is positioned inside the tank. The platform forms a water reservoir located beneath the platform. The platform has a top surface for placing the item to be treated An electrochemical generator is configured to generate the ozonated concentrate liquid from water. A circulating pump is configured to draw water from the water reservoir and supply the water to the electrochemical generator. A nozzle that is in fluid communication with the electrochemical generator. The nozzle is switchable between dispensing the ozonated concentrate liquid onto the item as the atomized mist or a spray. And, an egress port that is configured to drain the ozonated concentrate liquid from the top surface of the platform.

The method continues by treating the item with a spray of the ozonated concentrate liquid, in a wetting disinfecting manner, during treatments involving the atomized mist or the spray of the ozonated concentrate liquid onto the item. The egress port is configured to abate the accumulation of the ozonated concentrate liquid on the top surface of the platform.

The method continues by treating the item with an immersion in a purifying, deodorizing, and disinfecting manner, during treatments involving the immersion of the item in the ozonated concentrate liquid the nozzle is configured as the spray and the egress port is configured to allow the ozonated concentrate liquid to accumulate on the top of the platform immersing the item in the ozonated concentrate liquid. Upon completion of the immersion, the egress port is configured to discharge the ozonated concentrate liquid from the top surface of the platform.

Additional shortcomings of the prior art are overcome and additional advantages are provided through the provision of a method of transitioning an aqua-ozone hygienization system between a deodorizing atomized mist, a disinfection spray, and a purifying, deodorizing, and disinfecting immersion. The method comprises the steps of treating an item with an atomized mist of an ozonated concentrate liquid, in a non-wetting deodorizing manner.

The aqua-ozone hygienization system comprises a tank. A platform is positioned inside the tank. The platform forms a water reservoir located beneath the platform. The platform has a top surface for placing the item to be treated. An electrochemical generator that is configured to generate the ozonated concentrate liquid from water. A circulating pump is configured to draw water from the water reservoir and supply the water to the electrochemical generator. A nozzle that is in fluid communication with the electrochemical generator. The nozzle is switchable between dispensing the ozonated concentrate liquid onto the item as the atomized mist or a spray, and an ingress port is configured to allow water to fill the water reservoir.

The method continues by treating the item with a spray of the ozonated concentrate liquid, in a wetting disinfecting manner, during treatments involving the atomized mist or the spray of the ozonated concentrate liquid onto the item the ozonated concentrate liquid is absent accumulation on the top surface of the platform.

The method continues treating the item with an immersion in a purifying, deodorizing, and disinfecting manner, during treatments involving the immersion of the item, water is added by way of the ingress port to the water reservoir, raising the water level to an immersion level above the platform, immersing the item on the platform, the circulating pump and the electrochemical generator are operated to dispense, by way of the nozzle, the ozonated concentrate liquid into the tank mixing with the water creating a mixture until a desired ozone concentration of the mixture is achieved.

Additional shortcomings of the prior art are overcome and additional advantages are provided through the provision of a method of transitioning an aqua-ozone hygienization system between a deodorizing atomized mist, a disinfection spray, and a purifying, deodorizing, and disinfecting immersion. The method comprises the steps of treating an item with an atomized mist of an ozonated concentrate liquid, in a non-wetting deodorizing manner.

The aqua-ozone hygienization system comprises a tank. A platform is positioned within the tank. The platform in an extended position forms a water reservoir which comprises water located beneath the platform and in a retracted position the platform is immersed in the water within the water reservoir. The platform has a top surface for placing the item to be treated. An electrochemical generator that is configured to generate the ozonated concentrate liquid from water. A circulating pump that is configured to draw water from the water reservoir and supply the water to the electrochemical generator, and a nozzle that is in fluid communication with the electrochemical generator. The nozzle is switchable between dispensing the ozonated concentrate liquid onto the item as the atomized mist or a spray.

The method continues by treating the item with a spray of the ozonated concentrate liquid, in a wetting disinfecting manner, during treatments involving the atomized mist or the spray of the ozonated concentrate liquid onto the item the platform is in the extended position and the ozonated concentrate liquid is absent accumulation on the top surface of the platform.

The method continues by treating the item with an immersion in a purifying, deodorizing, and disinfecting manner, during treatments involving the immersion of the item, the platform is in the retracted position lowering the item into and immersing the item in the water reservoir. The circulating pump and the electrochemical generator are operated to dispense, by way of the nozzle, the ozonated concentrate liquid into the tank mixing with the water creating a mixture until a desired ozone concentration of the mixture is achieved.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIGS. 1-2 illustrate examples of an aqua-ozone hygienization system;

FIG. 3 illustrates one example of a system block diagram for an aqua-ozone hygienization system;

FIG. 4 illustrates one example of a control system for an aqua-ozone hygienization system;

FIG. 5 illustrates one example of transitioning an aqua-ozone hygienization system between a deodorizing atomized mist, a disinfection spray, a portable spray, and a purifying, deodorizing, and disinfecting immersion;

FIG. 7 illustrates one example of an aqueous ozone generator;

FIGS. 12-15 illustrates examples of methods of transitioning an aqua-ozone hygienization system between a deodorizing atomized mist, a disinfection spray, and a purifying, deodorizing, and disinfecting immersion.

Figure 1:
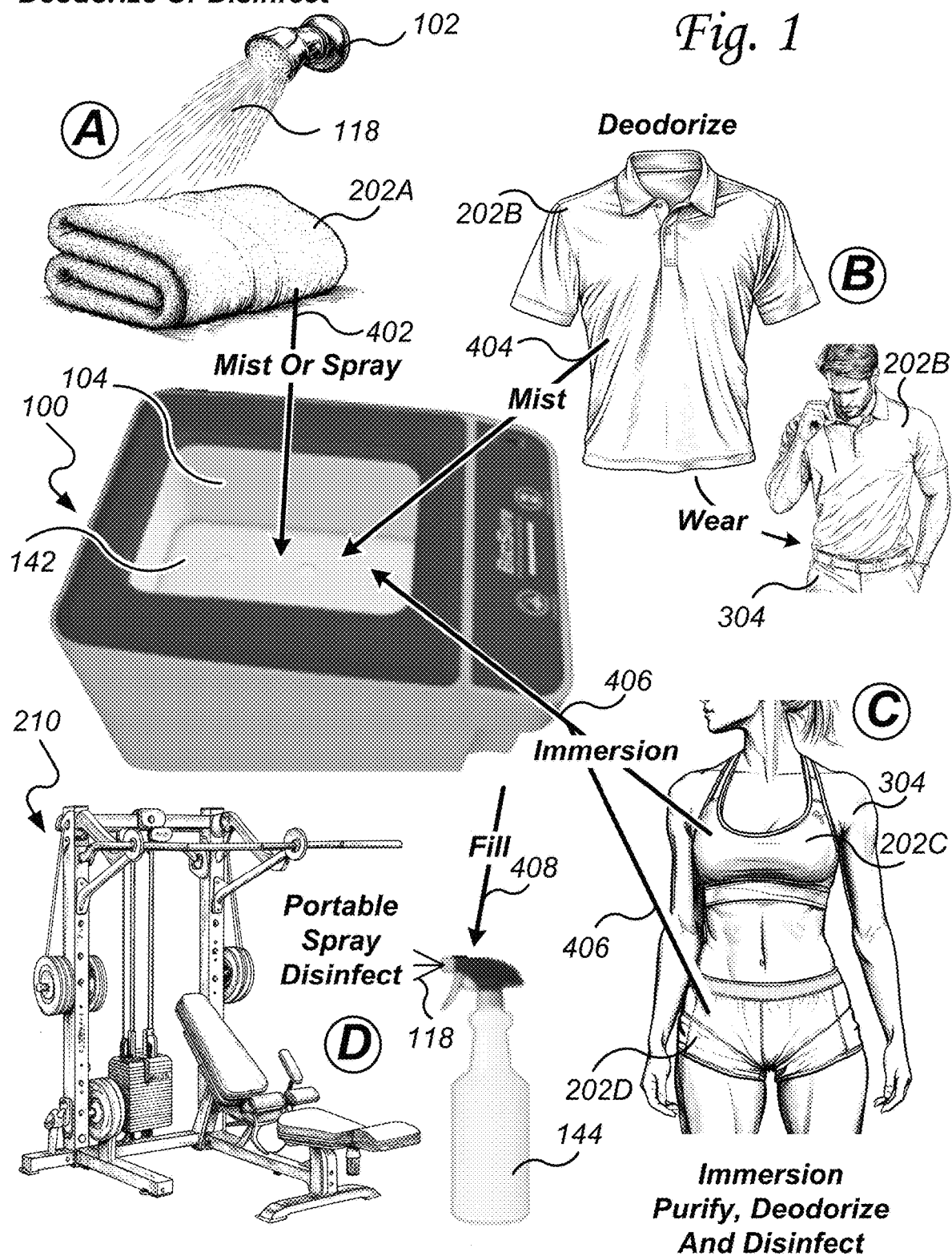

The detailed description explains the preferred embodiments of the invention, together with advantages and features, by way of example with reference to the drawings.

DETAILED DESCRIPTION OF THE INVENTION

The present invention elates to an aqua-ozone hygienization system and methods of use. In an exemplary embodiment, the present invention cleaning system is scientifically advanced using water infused with ozone, a powerful natural oxidizer, to achieve high levels of cleanliness and hygiene. The system works by delivering ozonated water, referred to as ozonated concentrate liquid, through different methods atomized misting (in a non-wetting manner), spraying (in a wetting manner), or immersion (in a soaking manner). Each method is tailored to specific purifying, deodorizing, and disinfection needs.

Atomized Misting: Provides a fine spray of ozonated concentrate liquid that can deodorize and freshen surfaces or fabrics without making them too wet. In this regard, such surfaces and fabrics after treatment can be immediately used or worn.

Spraying: Applies a more substantial amount of ozonated concentrate liquid to thoroughly disinfect and sanitize surfaces or materials, ensuring harmful bacteria and germs are eliminated.

Immersion: Involves purifying items in ozonated concentrate liquid, allowing for deep cleaning and disinfection that removes odors, sweat, and other contaminants.

An advantage of the present invention is that it leverages the natural disinfecting power of ozone-infused water, making it an effective and versatile solution for maintaining cleanliness and hygiene in various environments. Furthermore, the ozone is produced from water by way of an electrochemical generator which increases the purity level of the ozone produced (in excess of 20%) and eliminates harmful nitrogen species compounds that are produced from corona discharge-created ozone gas.

In the present invention, the term "hygienization" is intended to mean a comprehensive process aimed at improving the cleanliness and safety of a surface, a textile item, other items, or environment. This process typically involves:

Sanitizing: Reducing the number of harmful microorganisms to a safe level;

Deodorizing: Eliminating or neutralizing unpleasant odors caused by bacteria, mold, or other sources; and Disinfecting: Killing or inactivating pathogens, including bacteria, viruses, and fungi, to prevent the spread of illness.

When aqueous ozone is used for hygienization, it acts as a powerful agent that not only reduces the microbial load but also removes odors and destroys pathogens, resulting in thoroughly cleaned items and safe environments. The term hygienization emphasis both cleanliness and health, ensuring that the treated items and areas are hygienic, fresh, and free from harmful contaminants.

In the present invention, the term "aqua-ozone hygienization" and its design as a system and methods of use are intended to mean a multifunctional cleaning system that employs aqueous ozone-created ozonated water, referred to as ozonated concentrate liquid, to achieve comprehensive hygiene through various application methods. The system allows for precise control of ozonated concentrate liquid delivery, enabling it to be atomized misted, sprayed, or used in immersion, depending on the specific hygiene requirement.

Turning now to the drawings in greater detail, it will be seen that in FIGS. 1 and 2 there is illustrated one example of an aqua-ozone hygienization system 100. In an exemplary embodiment, for example, and not a limitation, a fitness center use case is used to illustrate the different methods of treatment in the present invention. The aqua-ozone hygienization system 100 can be used in other exemplary embodiments, areas, and environments without limitation. Such other use cases can be factories, warehouses, auto shops, laundromats, retail stores, home use, locker rooms, and numerous other uses, locations, and environments, as may be required and or desired in a particular embodiment.

In an exemplary embodiment, of use in a fitness center 210:

Towel 202A Treatment: Towel 202A can be placed 402 in the aqua-ozone hygienization system 100. The towel 202A can then be atomized and misted with ozonated concentrate liquid 118, allowing them to remain mostly dry and immediately useable while neutralizing odors. Alternatively, towels 202 can be sprayed to become damp, effectively disinfecting them by killing bacteria and other pathogens. As an example, user 304 may atomize mist the towel 202A before workout and use it so the towel is fresh and deodorized. Then after the workout and use of the towel wiping sweat from user 304 or exercise equipment 210, user 304 can spray the towel for a more comprehensive disinfection.

Workout Clothes 202C-D Treatment: Workout clothes 202C-D can be placed 406 in the aqua-ozone hygienization system 100. The Sweaty workout clothes 202C-D can then be immersed in ozonated concentrate liquid 118, allowing them to be purified, rinsed, deodorized, and disinfected, leaving them fresh, clean, and odor-free.

Post-Workout Clothing 202B Treatment: After a workout, a shirt or blouse 202B can be placed 404 in the aqua-ozone hygienization system 100. Such clothing can then be misted with ozonated concentrate liquid 118 in a non-wetting manner. This treatment keeps the fabric mostly dry while deodorizing it, ensuring that the clothing doesn't smell like the gym and is ready for immediate wear, whether to the office, school, home, or other occasions.

Fitness Equipment Treatment: A spray bottle 144 can be filled with ozonated concentrate liquid 118 and then sprayed, in a sanitizing manner, onto the fitness equipment and other surfaces. Such fitness equipment 210 can be weights, treadmills, yoga mats, and other fitness equipment after each use, ensuring a clean and safe environment for all users 304.

For disclosure purposes, towels 202A, shirts or clothing 202B, workout clothing 202C-D, and other items can all be referred to as item 202. As such item 202 can be placed in the aqua-ozone hygienization system 100 for treatment.

An advantage of the present invention is that it is designed to adapt to various cleaning needs within the fitness center and numerous other environments, providing a versatile, ozone-powered solution for maintaining high standards of hygiene and cleanliness. In this regard, a multi-step process aimed at achieving a high standard of environmental cleanliness by utilizing chemical and physical methods to reduce, inactivate, or eliminate harmful microorganisms, pathogens, and organic compounds. In an aqua-ozone hygienization system 100, this process relies on the properties of ozonated water (water infused with ozone ($O_3$) created by an electrochemical generator), to achieve its effects.

Scientific Basis:

Ozone as an Oxidizing Agent: Ozone is a triatomic molecule consisting of three oxygen atoms. It is a powerful oxidizing agent, meaning it can readily react with and break down the cell walls of bacteria, viruses, and other pathogens. When ozone comes into contact with organic matter or microorganisms, it oxidizes its cellular components, leading to the rupture of cell walls and the subsequent inactivation or death of the organism.

Ozonated Water: Also referred to as ozonated concentrate liquid 118, in the aqua-ozone hygienization system 100, ozone is generated, by way of an electrochemical generator 516, in water, creating a potent cleaning solution. The ozonated concentrate liquid 118 retains the oxidizing properties of ozone while being safer and easier to handle than ozone gas and absent dangerous nitrogen species of compounds produced by corona discharge methods. The aqueous ozone acts upon contact, breaking down contaminants, neutralizing odors, and disinfecting surfaces.

Application Methods:

Misting: Delivers a fine spray of ozonated water onto item 202 surface, allowing for broad surface coverage without significant moisture buildup. This is effective for deodorizing and lightly sanitizing surfaces where maintaining dryness is important.

Spraying: Involves a more concentrated application of ozonated water, which wets the surface of item 202 more thoroughly, allowing for deeper penetration into contaminants. This is particularly useful for disinfecting and removing more stubborn microorganisms.

Immersion: Items 202 are fully submerged in ozonated water, ensuring comprehensive contact with the solution. This method is ideal for deeply embedded contaminants or for items that require a more intensive cleaning process.

Chemical Reactions:

When ozone ($O_3$) encounters organic materials or pathogens, it oxidizes them, typically resulting in the formation of oxygen ($O_2$) and harmless byproducts such as carbon dioxide ($CO_2$) or water ($H_2O$). The breakdown of these materials leads to effective deodorization, sanitization, and disinfection, as the underlying causes of odors and contamination are chemically neutralized.

Benefits:

Broad-Spectrum Efficacy: Ozonated concentrate liquid 118 is effective against a wide range of microorganisms, including bacteria, viruses, fungi, and protozoa.

Eco-Friendly: The use of ozone leaves no harmful residues, as it naturally decomposes back into oxygen after reacting, making it an environmentally friendly option.

Versatility: The ability to mist, spray, or immerse items in ozonated water allows for tailored hygienization based on specific needs, ensuring optimal results across different scenarios.

With reference to at least FIGS. 1 and 2, in an exemplary embodiment, an aqua-ozone hygienization system 100 can comprise a tank 104 that is configured to hold item 202 for hygienization. Hygienization is effectuated by way of user 304 selecting between treating item 202 with an atomized mist in a non-wetting deodorizing manner, a spray in a wetting disinfecting manner, or an immersion in a purifying, deodorizing, and disinfecting manner.

The aqua-ozone hygienization system 100 can further comprise a platform positioned 142 within tank 104. Platform 142 forms a water reservoir 140 located beneath platform 142. Platform 142 has a top surface for placing item 202 to be treated.

The aqua-ozone hygienization system 100 can further comprise an electrochemical generator 516 that is configured to generate an ozonated concentrate liquid 118 from water. A circulating pump is configured to draw water from the water reservoir 140 and supply the water to the electrochemical generator 516. A nozzle 102 that is in fluid communication with the electrochemical generator 516. The nozzle 102 can be switched between dispensing the ozonated concentrate liquid 118 onto item 202 as the atomized mist or as the spray. An egress port 162 is configured to drain the ozonated concentrate liquid 118 from the top surface of platform 142.

In operation, during treatments involving the atomized mist or the spray of the ozonated concentrate liquid 118 onto item 202, the egress port 162 can be configured to abate accumulation of the ozonated concentrate liquid 118 on the top surface of the platform 142. And, during treatments involving the immersion of item 202 in the ozonated concentrate liquid 118, nozzle 102 can be configured as the spray and the egress port 162 can be configured to allow the ozonated concentrate liquid 118 to accumulate on the top of the platform 142 immersing the item 202 in the ozonated concentrate liquid 118. Upon completion of the immersion, the egress port 162 can be configured to discharge the ozonated concentrate liquid 118 from the top surface of the platform 142.

Referring to FIG. 2, there are illustrated examples of an aqua-ozone hygienization system 100. In an exemplary embodiment, in reference 'A' there is illustrated an aqua-ozone hygienization system 100 comprising a control panel 106 and an external nozzle 122.

Reference 'B' better illustrates the control panel 106. In an exemplary embodiment, a user interface also referred to as a control panel 106 for the aqua-ozone hygienization system 100 can comprise at least one of the following a display 506, a display 506 with touchscreen, a communication interface 508 configured to data communicate with a remote data processing resource 702 such as a server 702 and/or a computing device 732.

The control panel 106 for the aqua-ozone hygienization system 100 can further comprise a plurality of button input capabilities by way of the GPIO 510, or other user interfaces. The user interface is operationally related to the microcontroller 502

In an exemplary embodiment, one such button can be a deodorize/disinfect button 110. Such a button 110 can be used to initiate treatment cycles for items placed on the platform 142.

Another such button can be the ozonated concentrate liquid release button 124. Such ozonated concentrate liquid release button 124 can initiate the dispensing of ozonated concentrate liquid from the external nozzle 122. In this regard, an external nozzle 122 can be positioned external to tank 104 and can be configured to fill an external vessel 144.

Additionally, a light bar/display 112, a battery charge indicator 116 (for battery operation), and a power port 126 for recharging batteries can be included. Such light bar/display 112 can be used to indicate states of operation through color change, flashing, text display, or other suitable methods. Such features can be part of display 506. General purpose inputs/outputs (GPIO) 510, power supply 526, or other suitable integrations with control system 500, as may be required and/or desired in a particular embodiment.

In another exemplary embodiment, and with reference to reference 'C', an external nozzle 122 can be positioned within a concave portion 120 and configured to fill an external vessel 144 with the ozonated concentrate liquid 118. Tank 104 comprises the concave portion 120 along the exterior surface. The external vessel 114 fits and is storable, in a removable manner, within the concave portion 120. An overhang roof 154 can be part of the concave portion 120 to aid in positioning the external nozzle 122 to efficiently fill external vessel 114 with ozonate concentrate liquid 118.

Referring to FIG. 3, there is illustrated one example of a system block diagram for an aqua-ozone hygienization system 100. In an exemplary embodiment, an aqua-ozone hygienization system 100 can comprise a tank 104 that is configured to hold item 202 for hygienization. Hygienization can be effectuated by way of user 304 selecting between treating the item with an atomized mist in a non-wetting deodorizing manner, a spray in a wetting disinfecting manner, or an immersion in a purifying, deodorizing, and disinfecting manner.

Platform 142 can be positioned within tank 104. Platform 142 can form a water reservoir 140 located beneath platform 142. Platform 142 can have a top surface for placing item 202 to be treated. An electrochemical generator 516 can be configured to generate an ozonated concentrate liquid 118 from water 114. A circulating pump 128B can be configured to draw water 114 from the water reservoir 140 and supply the water 114 to the electrochemical generator 516.

Nozzle 102 can be in fluid communication with the electrochemical generator 516. Nozzle 102 can be switchable 132 between dispensing the ozonated concentrate liquid 118 onto the item as the atomized mist or as the spray. In this regard, to switch between the atomized mist and spray, nozzle 102 can be mechanically changed (manually by user 304 or automatically by control system 500), the ozonated concentrate liquid 118 can be routed to different apertures in nozzle 102, the nozzle 102 can comprise more than one sub-nozzles-some atomized mist and some spray, valves can be controlled by the control system 500/valve control 524 to switch flow routes or direct flow to different sub nozzles, or other suitable methods can be implemented, as may be required and/or desired in a particular embodiment.

An ingress port 164 can be configured to allow water 114 to fill the water reservoir 140. In an exemplary embodiment is the water source 114 is under sufficient pressure a pump 128A may not be needed. In such a configuration, a bypass 146 can be used. Otherwise, in low and no water pressure situations a pump 128A can utilized. Additionally, in some exemplary embodiment, a portion of the water supply 114 can be routed 148 to the input of the circulating pump 128B or alternatively routed 146 directly to the electrochemical generator 516. Valves 130C-D can be used to manage the flow of water 114 through out the system, as required and/or desired in a particular embodiment.

In an exemplary embodiment, in operation, during treatments involving the atomized mist or the spray of the ozonated concentrate liquid 118 onto the item the ozonated concentrate liquid can be absent accumulation on the top surface of the platform 142. And, during treatments involving the immersion of item 202, water 114 can be added by way of the ingress port 164 to the water reservoir 140, raising the water level 410 to an immersion level 412 above platform 142, immersing item 202 that is placed on platform 142. The circulating pump 128B and the electrochemical generator 516 can be operated 416 (drawing water 114 from the water reservoir 140, producing ozonated concentrate liquid 118, and dispensing the ozonated concentrate liquid 118 into tank 104) to produce and dispense, by way of the nozzle 102, the ozonated concentrate liquid 118 into tank 104 mixing with water 114 creating a mixture 114/118 until a desired ozone concentration 420 of the mixture 114/118 is achieved. With reference to at least FIGS. 4 and 6, reference 'D', an ozone concentration sensor 522 can be configured to determine the ozone concentration level 420 of the ozonate concentrate liquid 118.

In an exemplary embodiment, the electrochemical generator 516 can further comprise an ion exchange material 534. Additionally, a consumables cartridge 158 can be inserted, in a removable manner, into the aqua-ozone hygienization system 100. The consumables cartridge can comprise the electrochemical generator 516 as well as the ion exchange material 534 and other consumables. In this regard, as the consumables are consumed over time during the use of the aqua-ozone hygienization system 100, it is easy for a technician 302 to easily unscrew 134 or otherwise unfastened, remove, and replace the consumables cartridge 158 to keep the aqua-ozone hygienization system 100 operating efficiently.

In an exemplary embodiment, an egress port 162 can be positioned to discharge 136 the ozonated concentrate liquid 118, water 114, of the mixture 114/118 at the platform level 162A and/or the water reservoir level 162B. Valves 130E-F can be used to control the discharge 136, as may be required and/or desired in a particular embodiment. Additionally, valves 130A-B can be used to control the flow of the ozonated concentrate liquid 118, as may be required and/or desired in a particular embodiment.

In an exemplary embodiment, a control system 500 can comprise a microcontroller 502, a memory 504, and a liquid level sensor 518. The microcontroller 502 can be operationally related to the memory 504 and the liquid level sensor 518. The memory 504 can be encoded with instructions that when executed by the microcontroller 502 perform the steps of closing the egress port 130E-F/162A-B. Placing nozzle 102 in the spray mode of operation, operating the circulating pump 128B and the electrochemical generator 516, causing the ozonated concentrate liquid 118 to be produced and dispensed into tank 104. Stopping the circulating pump 128B and the electrochemical generator 516 when the liquid level sensor 518 determines that an immersion level 412 within tank 104 of the ozonated concentrate liquid 118 has been achieved. Delaying an immersion time period with item 202 immersed in the ozonated concentrate liquid to effectuate purification, deodorization, and disinfection of item 202. And, opening the egress port 130E-F/162A-B after the immersion time period elapses, allowing the ozonated concentrate liquid 118 to be discharged 136 from tank 104. Such immersion time period can be in the range of 5 to 60 seconds, or other desired range as may be required and/or desired in a particular embodiment.

Referring to FIG. 4, there is illustrated one example of a control system 500 for the aqua-ozone hygienization system 100. In an exemplary embodiment, control system 500 can be integrated into and be responsive to the action of an aqua-ozone hygienization system 100. In addition, control system 500 can be a web-enabled control system.

The term "web-enabled" or "web-enabled control system" or "web-enabled control system 500" in the present invention is intended to mean an Internet-of-things device. In this regard, a device that is capable of connecting a physical device such as an aqua-ozone hygienization system 100 to the digital world. Stated differently, web-enabling is equipping a device with the necessary electronics to be monitored, and controlled, and data communicate locally and remotely with other data-communicating devices. Such other data-communicating devices can be smartphones, tablets, laptops, mobile communication devices, other web-enabled devices, remote data processing resources, servers, and similar devices.

Figure 8:
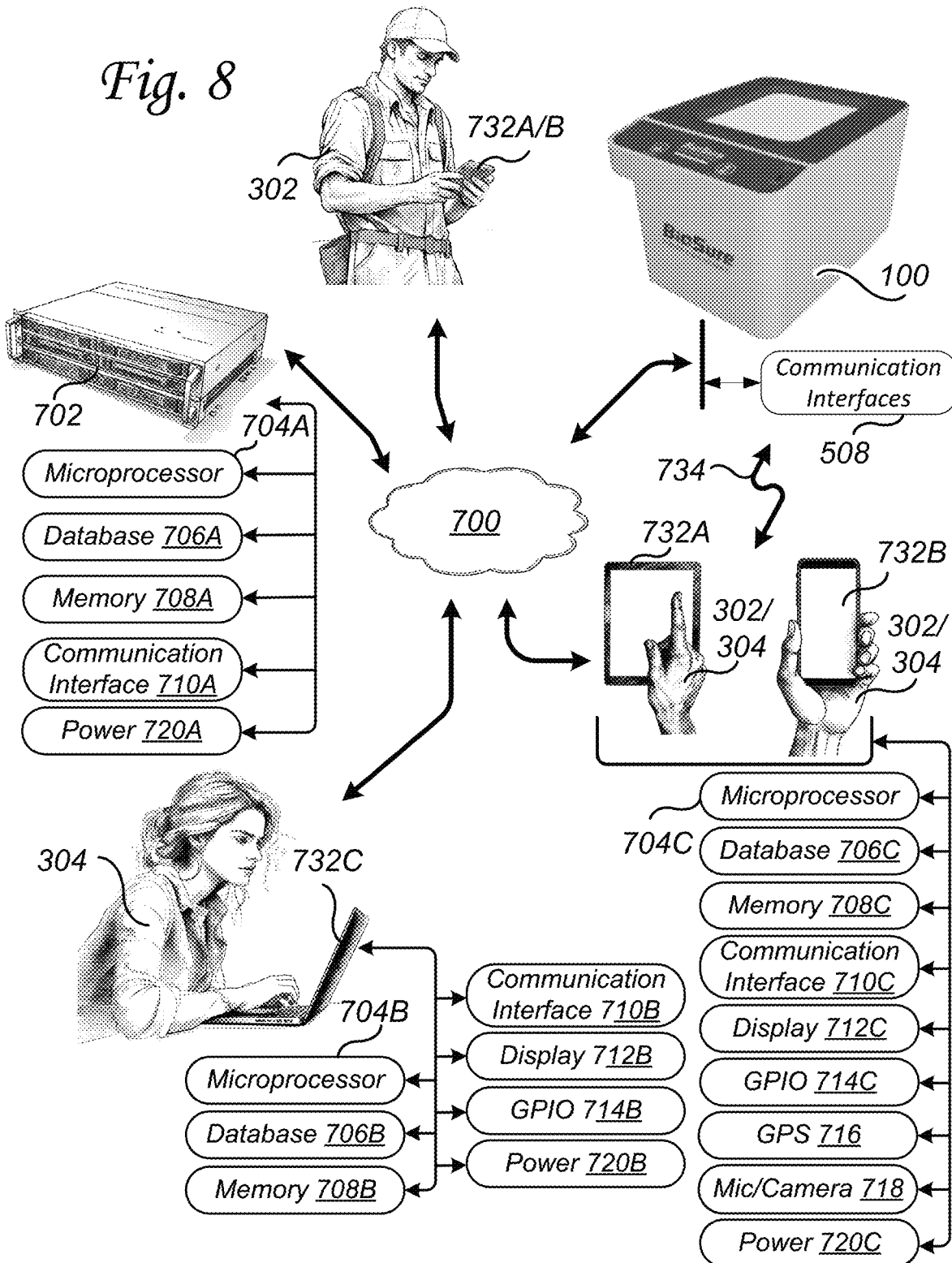
FIG. 8 illustrates one example of a system and network diagram.

In addition, and with reference to at least FIG. 8, such data communicating devices 732 can data communicate with remote data processing resources 702 and store and retrieve data from databases 706A-C, and other data processing resources, as may be required and/or desired in a particular embodiment. Laptops, smartphones, smartwatches, tablets, desktop computers, servers, mobile communication devices, and other types and kinds of data communication devices can all be data communicating devices 732 also referred to as computing devices 732.

In operation, a technician 302, an administrator 304, or other authorized people can use computing device 732 to interact with the aqueous ozone generator 530 or aqua-ozone hygienization system. The aqueous ozone generator 530 can comprise the electrochemical generator 516 and ion exchange material 534.

In this regard, a technician 302 can be a person who operates, maintains, cleans, configures, repairs and performs other functions on or with the aqueous ozone generator 530 or aqua-ozone hygienization system 100. An administrator 304 can be a person who administers, provides remote service or technical support, or be other types or kinds of authorized user, as may be required and/or desired in a particular embodiment.

In operation the control system 500, by way of the communication interface 508 can data communicate with remote data processing resources 702. Such remote data processing resources 702 can be servers or other types or kinds of data processing resources. Furthermore, data communicating devices 732, remote data processing resources 702, data storage resources 706A-C, and other types and kinds of data communicating devices can data communicate over a global network 700. The Internet is a global network 700.

In an exemplary embodiment and with reference to at least FIG. 4, the aqua-ozone hygienization system 100 can be equipped with a web-enabled control system 500. Such a web-enabled control system 500 can comprise a microcontroller 502 which is operationally related to a memory 504, a display 506, a plurality of communication interfaces 508, general purpose input and outputs (GPIO) 510, a plurality of sensors 512, a global position system (GPS) 514, an electrochemical generator 516, a liquid level sensor 518, a pump controller 520 that is operationally related to a plurality of pumps/valves 128, a plurality of ozone sensors 522, a valve controller 524, a power supply 526, current sensor 528, an aqueous ozone generator 530, and a water heater 536.

The microcontroller 502 can be INTEL, ZILOG, MICROCHIP, AMD, ARM, and/or other types or kinds of microcontrollers.

The memory 504 can be a combination of random access memory (RAM), read-only memory (ROM), flash, hard drives, solid-state drives, USB flash drives, and/or other types and kinds of memory.

The display 506 can be a liquid crystal display (LCD), organic light emitting diode (OLED), or light emitting diode (LED), as well as have touch input capabilities and/or other types and kinds of displays and user inputs as may be required and/or desired in a particular embodiment.

The communication interface 508 can be LAN, WAN, USB, Ethernet, RS232, RS485, serial, WiFi, 802.11abgn and similar, second-generation (2G), third-generation (3G), fourth-generation (4G), or fifth-generation (5G) compatible, Bluetooth, TCP, UDP, Mesh Network, Zigbee, Pico Network, LORAN, and/or other types and kinds of communication interfaces and protocols.

In an exemplary embodiment, the communication interface 508 is operationally related to the microcontroller 502. The control system 500, by way of the communication interface 508, data communicates with the remote data processing resource 702, data communication devices 732, and other data processing resources in a local area network environment or a wide area network environment across a global network 700 in a wired or wireless manner as may be required and/or desired in a particular embodiment. The Internet is a global network 700.

In an exemplary embodiment, the control system 500 can comprise a microcontroller 502, a memory 504, and a communication interface 508. The microcontroller 502 can be operationally related to the memory 504 and the communication interface 508. The memory 504 can be encoded with instructions that when executed by the microcontroller 502 perform the step of sending an operational status message by way of the communication interface 508 to a remote data processing resource 702. Such an operational status message can be related to the operational performance of the electrochemical generator 516. Additionally, the control system 500 further comprises a global position system (GPS) 514 that can be operationally related to the microcontroller 502. In operation, the operational status message can be related to the GPS location of the aqua-ozone hygienization system 100. In a plurality of other exemplary embodiments, the operational status message can be related to other operational, performance, and other data or conditions as may be required and/or desired in a particular embodiment.

The GPIO 510 can be transistor-to-transistor (TTL), complementary metal-oxide-semiconductor (CMOS), transistors, buffers, relays, pushbuttons, switches, and/or other types and kinds of GPIO circuits.

The sensors 512 and/motion sensor 518 can be passive infrared (PIR) motion sensors, infrared, thermal, Doppler radar, ultrasonic, capacitance, touch-type, optical, Hall effect, switch, fingerprint, and other types of biometric sensors, and/or other types and kinds of sensors. Additionally, sensor 512 can be ambient condition sensors such as temperature, moisture, humidity, total dissolved solids (TDS), sunlight, and/or other types and kinds of sensors.

In an exemplary embodiment, analog-type sensor determinations can be converted to digital values so that the microcontroller 502 can process the data. Alternatively, the microcontroller 502 can perform analog-to-digital conversions if equipped to perform such functions.

The electrochemical generator 516 can be an electrolysis-based device that utilizes ion exchange material 534 and other devices and processes to produce chemical compounds from water such as ozone $O_3$.

The liquid level sensor 518 can be utilized to determine the water 114 level in the water reservoir 140, the ozonated concentrate liquid 118 accumulated in tank 104, mixture 114/118 of water 114 and the ozonated concentrate liquid 118 in tank 104, or other suitable liquid levels, as may be desired and/or desired in a particular embodiment.

The pumps and/or valves 520, in addition to performing their fluid handling tasks, pumps and/or valves 520 can be actuated and/or controlled by way of a relay, metal-oxide-semiconductor field-effect transistor (MOSFET), or other types and kinds of controlling devices. In addition, valve controller 524 and operationally related to valves/actuators 130 (better illustrated in at least FIG. 3 as valves 130A-F) such as solenoids, and other fluid management devices can be integrated into the system, as may be required and/or desired in a particular embodiment. Such valves/actuators 130 can be opened and closed to control the flow of water 114, ozonated concentrate liquid 118, discharge 136, and used in other ways to control other fluids or gases as may be required and or desired in a particular embodiment.

The ozone sensor 522 can be configured to monitor the ozone concentration supplied to the system or other sources of ozonated liquid, as may be required and/or desired in a particular embodiment.

The power supply 526 can be AC, DC, battery including rechargeable, solar, and/or other types and kinds of power supplies.

The current sensor 528 can be configured to measure the supplied electrical current to the electrochemical generator 516, the aqueous ozone generator 530, a combination 516/132 thereof, and/or other devices and systems, as may be required and/or desired in a particular embodiment.

The aqueous ozone generator 530 receives water as an input and uses the electrochemical generator 516 which is integrated into the aqueous ozone generator 530 to produce high concentrations of aqueous ozone molecules. Such concentrations of aqueous ozone can range from 1 ppm to 10 ppm or other desired range, as may be required and/or desired in a particular embodiment.

The water heater 538 can be a resistive type or other suit type of water heater. In an exemplary embodiment, the water heater 538 can be configured to warm the water 114 in the water reservoir 140. In this regard, as users 304 interact with and touch the water 114 and ozonated concentrate liquid 118, the water can be warmed to a comfort level making the experience more enjoyable for the user 304.

In an exemplary embodiment, a user interface also referred to as a control panel 106 for the aqua-ozone hygienization system 100 can comprise at least one of the following a display 506, a display 506 with touchscreen, a communication interface 508 configured to data communicate with a remote data processing resource 702 such as a server 702 and/or a computing device 732.

The control panel 106 for the aqua-ozone hygienization system 100 can further comprise a plurality of button input capabilities by way of the GPIO 510, or other user interfaces. The user interface is operationally related to the microcontroller 502.

Referring to FIG. 5, there is illustrated one example of transitioning an aqua-ozone hygienization system between a deodorizing atomized mist, a disinfection spray, a portable spray, and a purifying, deodorizing, and disinfecting immersion.

In an exemplary embodiment, in the application of, for example, and not a limitation, item 202 treatment (such as towels, clothing, other textiles, or other suitable non-textile items), the present invention utilizes ozonated concentrate liquid 118, delivered in several distinct ways, each tailored for specific treatment needs:

Atomizing Mist: in reference 'A', the water level is low 410 typically confined to the water reservoir 140. The nozzle 102 is configured 132 for a finely atomized mist of the ozonated concentrate liquid 118. The ozonated concentrate liquid 118 is dispersed onto the surface of item 202, creating a non-wetting treatment. This method is ideal for deodorizing fabrics by neutralizing odors without significantly dampening the material, making it suitable for items that need to remain dry and ready for immediate use.

Spray Application: In reference 'B', the water level is low 410 typically confined to the water reservoir 140. The nozzle 102 is configured 132 for spraying the ozonated concentrate liquid 118. In this regard, a more concentrated spray of ozonated liquid is applied, resulting in a wetting effect on item 202. This method is designed for disinfecting fabrics by thoroughly wetting the surface, allowing the ozonated concentrate liquid 118 to penetrate and eliminate pathogens, bacteria, and other harmful microorganisms.

Immersion: In reference 'C', Textiles are fully submerged in the ozonated concentrate liquid 118, providing a comprehensive treatment that purifies, deodorizes, and disinfects in a wetting manner. This approach ensures deep cleaning by allowing the ozone to penetrate every fiber of the fabric, effectively removing contaminants, neutralizing odors, and eliminating harmful microorganisms. In an exemplary embodiment, item 202 on platform 142 is flooded to an immersion level 412. This can happen in a couple of different ways, three of which are illustrated below:

(1) The nozzle 102 can be configured 132 to spray and the egress port 130E-F/162 is configured to allow the ozonated concentrate liquid 118 to accumulate on the top of the platform 142 immersing item 202 in the ozonated concentrate liquid 118. Upon completion of the immersion, the egress port 130E-F/162 can be configured to discharge 136 the ozonated concentrate liquid 118 from the top surface of the platform 142;

(2) The nozzle 102 can be configured 132 to spray. Water 114 is added by way of the ingress port 164 to the water reservoir 140, raising the water 114 level to an immersion level 412 above platform 142, immersing item 202 on platform 142. The circulating pump 128B and the electrochemical generator 516 are operated to produce and dispense, by way of the nozzle 102, the ozonated concentrate liquid 118 into the tank 104 mixing with the water 114 creating a mixture 114/118 until a desired ozone concentration 420 of the mixture 114/118/422 is achieved; or (3) The nozzle 102 can be configured 132 to spray. Platform 142 with item 202 on top can be transitioned from an extended position 156A (as better illustrated in at least FIG. 6, reference 'B' platform 142A) to a retracted position 156B (as better illustrated in at least FIG. 6, reference 'B' platform 142B) lowering item 202 into and immersing item 202 in the water reservoir 14. The circulating pump 128B and the electrochemical generator 516 are operated to produce and dispense, by way of nozzle 102, the ozonated concentrate liquid 118 into the tank 104 mixing with water 114 creating a mixture 114/118 until a desired ozone concentration 42 of the mixture 114/118/422 is achieved.

Portable Spray: in reference 'D', a spray bottle 144 can be filled with ozonated concentrate liquid 118 and then sprayed, in a sanitizing manner, onto the surfaces and equipment, such a fitness equipment 210, and other equipment as an example, and not a limitation. Such fitness equipment 210 can be weights, treadmills, yoga mats, and other fitness equipment after each use, ensuring a clean and safe environment for all users 304.

These methods provide flexibility in treating items 202 of all types including textiles and non-textiles, depending on the desired outcome, whether it's maintaining dryness while deodorizing, achieving deeper disinfection with wetting, or fully purifying through immersion.

Figure 6:
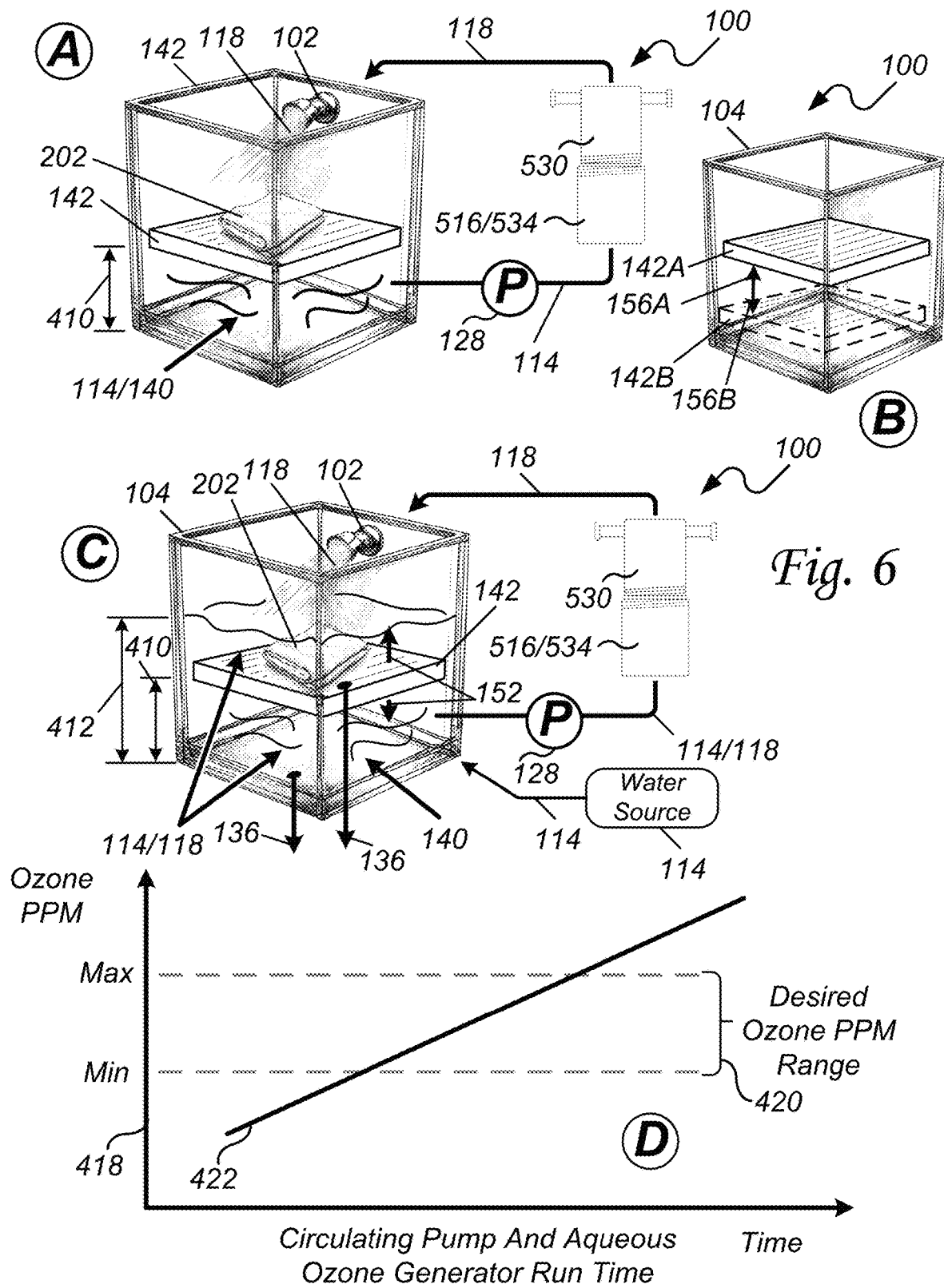
FIG. 6 illustrates examples of operating an aqua-ozone hygienization system.

Referring to FIG. 6, there are illustrated examples of operating an aqua-ozone hygienization system. In an exemplary embodiment, in reference 'A', the aqua-ozone hygienization system 100 comprises tank 104, and platform 142 is positioned inside tank 104. Platform 142 forms a water reservoir 140 located beneath platform 142. Platform 142 has a top surface for placing item 202 such as a towel, shirt, other clothing, or other suitable items to be treated. Aqueous ozone generator 530 can comprise electrochemical generator 516. Electrochemical generator 516 can be configured to generate the ozonated concentrate liquid 118 from water 114. Circulating pump 128 can be configured 416 to draw water 114 from the water reservoir 140 and supply water 114 to the electrochemical generator 516. Nozzle 102 can be in fluid communication with the electrochemical generator 516. Nozzle 102 can be switchable 132 between dispensing the ozonated concentrate liquid 118 onto item 202 as the atomized mist or a spray. Egress port 162/130E can be configured to drain 136 the ozonated concentrate liquid 118 from the top surface of platform 142. In this regard, in an exemplary embodiment, platform 142 can form a liquid barrier and prevent mixing between the water reservoir 140 and ozonated concentrate liquid dispenses onto the top surface of platform 140.

Treating item 202 with an immersion in a purifying, deodorizing, and disinfecting manner. During treatments involving immersion of item 202 in the ozonated concentrate liquid 118, nozzle 102 can be configured 132 as a spray, and the egress port 162/130E can be configured to allow the ozonated concentrate liquid 118 to accumulate on the top of platform 148 immersing item 202 in the ozonated concentrate liquid 118. Upon completion of the immersion, the egress port 162/130E can be configured to discharge 136 the ozonated concentrate liquid 118 from the top surface of platform 142.

In an exemplary embodiment, in reference 'B', the aqua-ozone hygienization system 100 comprises tank 104, and platform 142 is positioned within tank 104. Platform 142 in an extended position 142A extended, motion 156A, forms a water reservoir 140 which comprises water located beneath platform 142, and in a retracted position 142B retracted, motion 156B, platform 142 is immersed in the water 114 within the water reservoir 140. Platform 142 has a top surface for placing item 202 such as a towel, shirt, other clothing, or other suitable items to be treated. Aqueous ozone generator 530 can comprise electrochemical generator 516. Electrochemical generator 516 can be configured to generate the ozonated concentrate liquid 118 from water 114. Circulating pump 128 can be configured 416 to draw water 114 from water reservoir 140 and supply water 114 to the electrochemical generator 516. Nozzle 102 can be in fluid communication with the electrochemical generator 516. Nozzle 102 can be switchable 132 between dispensing the ozonated concentrate liquid 118 onto item 202 as the atomized mist or a spray.

Treating item 202 with an immersion in a purifying, deodorizing, and disinfecting manner. During treatments involving the immersion of item 202, platform 142 can be is the retracted position lowering item 202 into and immersing item 202 in the water in the water reservoir 140. Circulating pump 128 and the electrochemical generator 516 are operated 416 to dispense, by way of nozzle 102, the ozonated concentrate liquid 118 into tank 104 mixing with the water 114 creating a mixture 114/118 until a desired ozone concentration 420 of mixture 114/118/422 is achieved. Such ozone concentration 422 of the mixture 114/118 can be determined by way of ozone sensor 522, or other suitable devices or methods.

In an exemplary embodiment, in reference 'C', the aqua-ozone hygienization system 100 comprises tank 104, and platform 142 is positioned inside tank 104. Platform 142 forms a water reservoir 140 located beneath platform 142. Platform 142 has a top surface for placing item 202 such as a towel, shirt, other clothing, or other suitable items to be treated. Electrochemical generator 516 can be configured to generate the ozonated concentrate liquid 118 from water 114. Circulating pump 128 can be configured 416 to draw water 114 from the water reservoir 140 and supply water 114 to the electrochemical generator 516. Nozzle 102 can be in fluid communication with the electrochemical generator 516. Nozzle 102 can be switchable 132 between dispensing the ozonated concentrate liquid 118 onto item 202 as the atomized mist or a spray. Ingress port 164 can be configured to allow water 114 to fill the water reservoir 140.

Treating item 202 with an immersion in a purifying, deodorizing, and disinfecting manner. During treatments involving immersion of item 202, water 114 can be added by way of the ingress port 164 to the water reservoir 140, raising the water level 410, permeating 152 platform 142, to an immersion level 412 above platform 142, immersing item 202 on platform 142. Circulating pump 128 and the electrochemical generator 516 are operated 416 to dispense, by way of the nozzle 102, the ozonated concentrate liquid 118 into tank 104 mixing with water 114 creating a mixture 114/118 until a desired ozone concentration 420 of mixture 114/118/422 is achieved. In this regard, in an exemplary embodiment, platform 142 can be permeable 152 allowing an overfilling of the water reservoir level 410 to rise through platform 142, allowing the water level to reach an immersion level 412. Such ozone concentration 422 of the mixture 114/118 can be determined by way of ozone sensor 522.

In an exemplary embodiment, in FIG. 6, reference 'D' chart 418 illustrates the relationship between ozone concentration 422 of the mixture 114/118 of water 114 and ozonated concentrate liquid 118 in relationship to the system run time of the circulating pump 128 and the electrochemical generator 516. In this regard, as the system runs the ozonated concentrate liquid 118 is dispensed into tank 104. In immersion treatments that mix the water 144 and the ozonated concentrate liquid 118, in the tank, the ozone concentration 442 of the mixture 114/118/422 can be determined by way of ozone sensor 522, or other suitable devices or methods.

In an exemplary embodiment, during operation, the circulating pump 128 and the electrochemical generator 516 can be operated to produce and dispense, by way of the nozzle 102, the ozonated concentrate liquid 118 into the tank mixing with the water 114 creating a mixture 114/118 until a desired ozone concentration 420 of the mixture 114/18 is achieved. Such ozone concentration 422 of the mixture 114/118 can be determined by way of ozone sensor 522.

Referring to FIG. 7, there is illustrated one example of an aqueous ozone generator 530. In an exemplary embodiment, aqueous ozone production involves electrolysis and an ion exchange material 534 which consumes certain components and materials during the process. Thus, when the service life of the aqueous ozone generator 530 and/or electrochemical generator 516 is over the consumables 516/534 need to be replaced. To ease and speed consumable 516/534 exchange by technician 302 a plumbed housing 160 can be permanently plumbed or otherwise fastened in place and the aqueous ozone generator 530 comprising the consumables 516/534, screwed 132 on to or otherwise fastened 132, in a removable manner, to the plumbed housing 160. In this regard, the aqueous ozone generator 530 can be easily and quickly removed as a cartridge 158 and exchanged for a new aqueous ozone generator 530 and electrochemical generator 516/ion exchange material 534 when the consumables 516/534 need to be replaced.

An advantage, in the present invention, is that once the plumbed housing 160 is installed and the liquid lines connected, the liquid lines don't need to be removed or disconnected to change the aqueous ozone generator 530. This saves technician 302 time, and cost, and reduces the chance of creating leaks in the system by having to disconnect/reconnect liquid carrying hoses.

Another advantage, in the present invention, is how the outflow of the assembled unit 158/160 can be configured. In this regard, in reference 'A' the assembled unit 158/160 can be configured to produce an ozonated concentrate liquid 118, or in reference 'B' and as better illustrated in at least FIG. 3 configured to produce an outflow of an ozonated concentrate liquid 118 stream and a water 114 stream. These streams 114/118 can be mixed at the point of dispense or mixed in the air as they are sprayed from one or more of the nozzles 102/122, as may be required and/or desired in a particular embodiment.

In an exemplary embodiment, in operation, a plumbed housing 160 can be fastened in fluid communication pathways with the water source 114 and the ozonated concentrate liquid 118. An electrochemical generator 516 is integrated into the aqueous ozone generator 530. The electrochemical generator 516 comprises an ion exchange material 534. The aqueous ozone generator 530 is interchangeable and removably fastened to the plumbed housing 160 in a replaceable cartridge 158 manner.

In an exemplary embodiment, a consumables cartridge 158 can be inserted, in a removable manner, into the aqua-ozone hygienization system 100. The consumables cartridge 158 can comprise the electrochemical generator 516 and other consumable components such as the ion exchange material 534.

In an exemplary embodiment, an electrochemical generator 516 can be integrated into the aqueous ozone generator 530. The electrochemical generator comprises an ion exchange material 534. A computing device 732, operated by technician 302, can data communicate the test ozone concentration to a remote data processing resource 702, and receive from the remote data processing resource 702, by way of the computing device 732 a plurality of aqueous ozone generator service life data that corresponds to the remaining service life of the electrochemical generator 516.

Referring to FIG. 8, there is illustrated one example of a system and network diagram. In an exemplary embodiment, users of the platform and network can include technicians 302, administrators 304, or other authorized persons.

Each of the users uses computing devices 732A-C to data communicate over a global communication network 700 with one or more data processing resources 702. The computing devices 732A-C can be laptop computers, desktop computers, smartphones, tablets, or other types and kinds of computing devices, as may be required and/or desired in a particular embodiment. For disclosure purposes, computing devices 732A-C can be referred to as computing devices 732. Additionally, laptop and desktop types of computing devices 732 can be referred to as computing devices 712C, computing devices 732 such as smartphones can be referred to as computing devices 732B, and computing devices 732 such as tablets can be referred to as computing devices 732A. In operation, any of the users can use any of the types of computing devices 732A-C, without limitation to the type or kind of computing device 732, as may be required and/or desired in a particular embodiment. The global communication network 700 can be the Internet.

The computing devices 732 can comprise a microprocessor 704B/704C, a database 706B/706C, memory 708B/708C, a communication interface 710B/710C, a display 712B/712C, and a plurality of general-purpose inputs and outputs (GPIO) 714B/714C.

Additionally, mobile type of computing device 732A/732B (tablets, smartphones, and others) can comprise a global positioning system (GPS) 716, and a microphone and/or camera 718.

In general, computing devices 232 can be configured with other functions and features, as may be required and/or desired in a particular embodiment.

In an exemplary embodiment, the microprocessor 704B is operationally related to database 706B, memory 708B, communication interface 710B, display 712B, and GPIO 714B.

In an exemplary embodiment, the microprocessor 704C is operationally related to database 706C, memory 708C, communication interface 710C, display 712C, GPIO 714C, and if equipped, with GPS 716, and microphone and/or camera 718. The computing devices 732 each rely on a suitable power source 720B/720C which can include a rechargeable battery, external power supply, or other types and/or kinds of power sources.

Microprocessor 704B/704C can be INTEL, ZILOG, MICROCHIP, AMD, ARM, and/or other types or kinds of microprocessors.

Database 706B/706C can be SQL, MYSQL, MARIADB, ORACLE, MS ACCESS, network-accessible storage, flat files, a combination thereof, or other types and kinds of databases.

Memory 708B/708C can be a combination of RAM, ROM, flash, hard drives, solid-state drives, USB flash drives, micro-SD cards, or other types of removable memory, and/or other types and kinds of memory.

The communication interfaces 710B/710C can be local area network (LAN), wide area network (WAN), universal serial bus (USB), Ethernet, RS232, RS485, serial, Wi-Fi, 802.11abgn and similar, 2G 3G 4G 5G compatible, Bluetooth, transmission control protocol (TCP), user datagram protocol (UDP), Mesh Network, Zigbee, Pico Network, long-range navigation (LORAN), and/or other types and kinds of communication interfaces and protocols.

Display 712B/712C can be a liquid crystal display (LCD), light emitting diode (LED), organic light emitting diode (OLED), or other types and kinds of displays.

The general-purpose inputs and outputs (GPIO) 714B/714C can be TTL, CMOS, MOSFET, transistors, buffers, relays, pushbuttons, switches, and/or other types and kinds of GPIO circuits. In an exemplary embodiment, some of the GPIO 214 lines can be used to drive a touch screen input, biometric input devices, keyboards, and/or types and kinds of computing device input devices.

Global positioning system (GPS) device 716 can be used to determine the geographic location of technician 302 and others who are carrying a computing device 732 equipped with a GPS 716. In this regard, such computing devices 732 are typically mobile computing devices such as tablets 732A, smartphones 732B, and other similar types and/or kinds of mobile computing devices 732.

Microphone and/or camera 718 can be used to record audio, and video, and take pictures. In this regard, users 304/306 can use their computing devices equipped with a microphone and/or camera 718 to make digital media records that can be selectively shared as appropriate including on social media and other digital media outlet locations.

With reference to FIG. 8, the data processing resource 702 can be a server, network storage device, or other types and kinds of data processing resources. Such data processing resources can be AMAZON WEB SERVICES (AWS), MICROSOFT AZURE, or other types and kinds of hosted data processing resource services. For disclosure purposes, a remote data processing resource 702 can also be referred to as server 702.

The data processing resource 702 can comprise a microprocessor 704A, a database 706A, memory 708A, and a communication interface 710A. The microprocessor 704A is operationally related to database 706A, memory 708A, and communication interface 710A.

The microprocessor 704A can be INTEL, ZILOG, MICROCHIP, AMD, ARM, and/or other types or kinds of microprocessors.

The database 706A can be SQL, MYSQL, MARIADB, ORACLE, MS ACCESS, network accessible storage, flat files, a combination thereof, or other types and kinds of databases.

The memory 708A can be a combination of RAM, ROM, flash, hard drives, solid-state drives, USB flash drives, micro-SD cards, or other types of removable memory, and/or other types and kinds of memory.

The communication interfaces 710A can be LAN, WAN, USB, Ethernet, RS232, RS485, serial, Wi-Fi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

Figure 9:
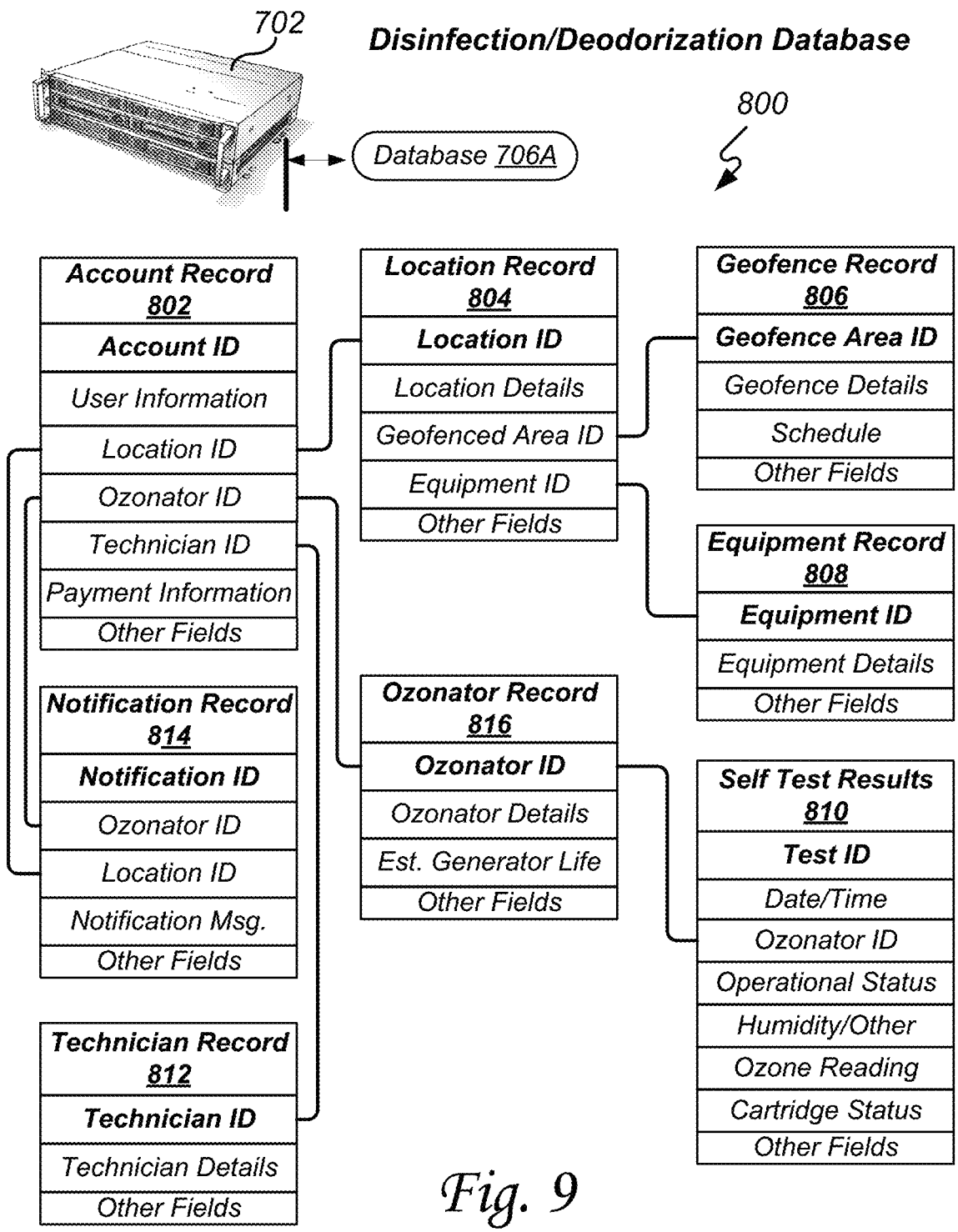
FIG. 9 illustrates one example of an ozone disinfection database structure.

Referring to FIG. 9, there is illustrated one example of an ozone disinfection/deodorization database structure 800. In an exemplary embodiment, at least one database 706A/706B/706C can be implemented on at least one of the data processing resources 702 also referred to as server 702, or computing devices 732. In operation, one or more databases 706A/706B/706C can be accessed/created/managed/maintained as appropriate by more than one stakeholder. In this regard, in addition to system administrators and other authorized persons, other stakeholders can access/create/manage/maintain as appropriate.

In an exemplary embodiment, such databases 706A/706B/706C can be SQL, MYSQL, MARIADB, ORACLE, MS ACCESS, network-accessible storage, flat files, a combination thereof, or other types and kinds of databases.

In an exemplary embodiment, the ozone disinfection/deodorization database 900 can reside on a remote data processing resource 702 in database 706A. In this regard, the ozone disinfection/deodorization database 800 can comprise a series of tables, records, fields, and accounts that include account record 802, location record 804, geofence record 806, equipment record 808, self-test results 810, technician record 812, notification record 814, ozonator record 816, and/or other types or kinds of records as may be required and/or desired in a particular embodiment. The database structure illustrated in FIG. 9 also illustrates some of the relationships between the various tables and fields.

In an exemplary embodiment, the data structure is illustrative and can be expanded and modified without particular limitation as needed and as appropriate to support the functionality and methods of the present invention and to support future functionality and methods of the present invention as it grows and evolves over time.

Figure 10:
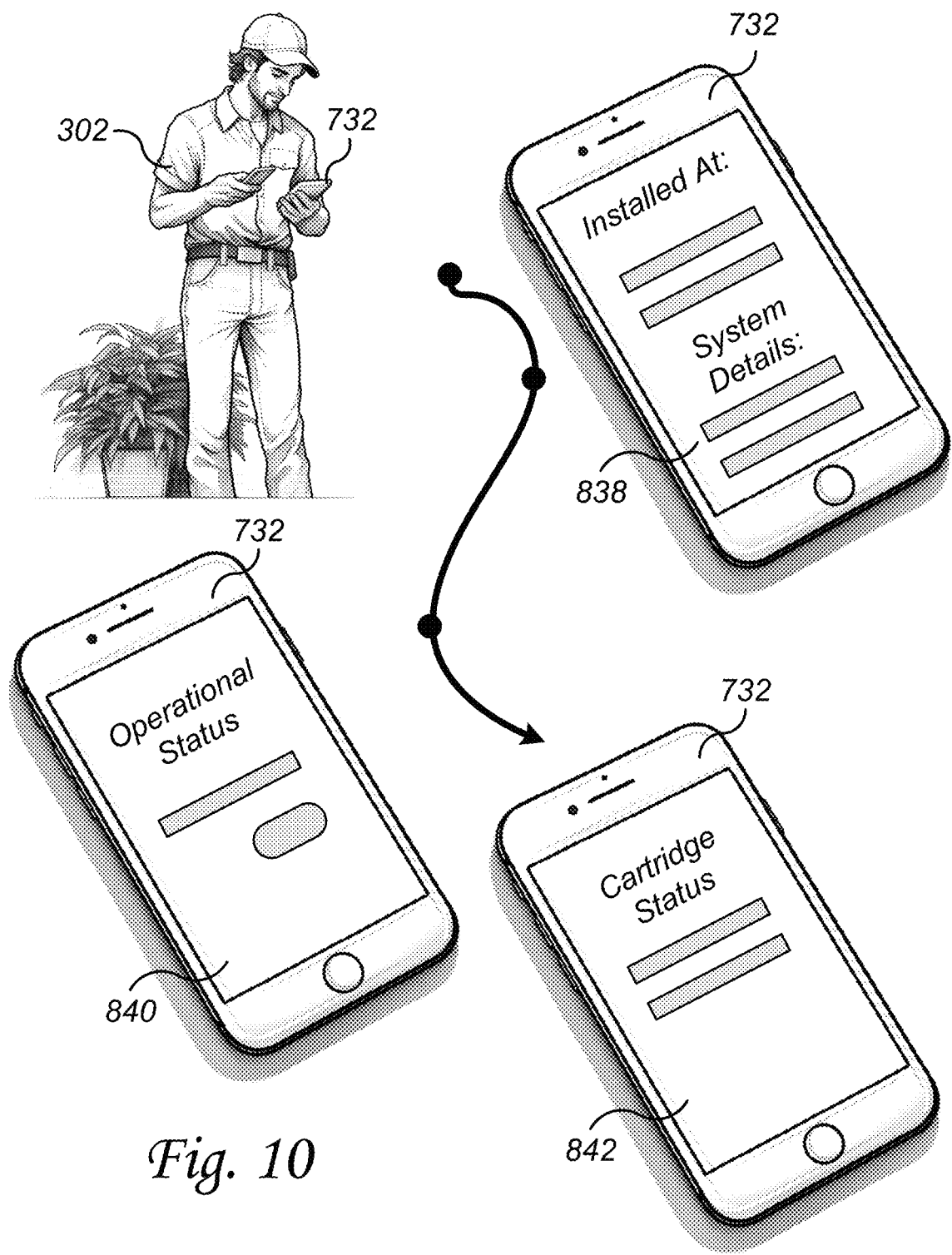
FIG. 10 illustrates one example of a technician's use of a software application.

Referring to FIG. 10, a technician's use of a software application. In an exemplary embodiment, a software application or website can be used in combination with the computing device 732A/B to identify the aqua-ozone hygienization system 100, view operational statuses, record the test results and other results, and see other useful data by way of data communicating with a remote data processing resource 702. In some embodiments, certain air deodorizing system 100 may have the ability to data communicate 734 directly with a remote data processing resource 702, eliminating the need for computing device 732A/B to act as an intermediary device to record test results on the remote data processing resource 702.

In an exemplary embodiment and with reference to at least FIG. 10, a computing device 732, operated by technician 302, data communicates with a remote data processing resource 702, and receives from the remote data processing resource 702, by way of the computing device 732 a plurality of aqua-ozone hygienization system 100 location 838 and service life data 840/842 that corresponds to the remaining service life the electrochemical generator 516 which can include the ion exchange material 534, and other service life information, as may be required and/or desired in a particular embodiment.

Figure 11:
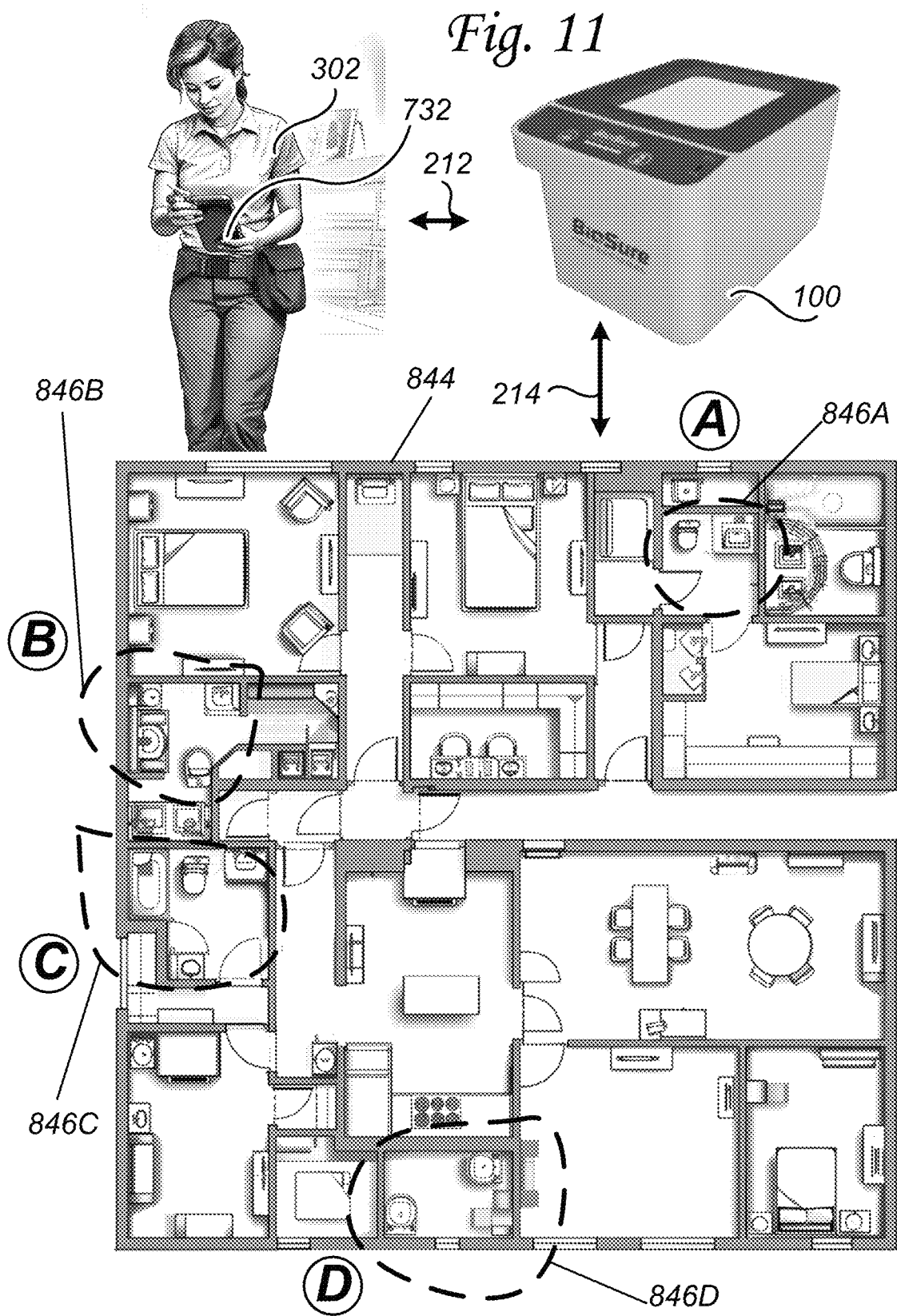
FIG. 11 illustrates one example of a floor plan to monitor geofenced or geolocate room spaces that have installed an aqua-ozone hygienization system.

Referring to FIG. 11, there is illustrated one example of a floor plan 844 to monitor geofenced or geolocate room spaces 'A' 846A, 'B' 846B, 'C' 846C, and 'D' 846D that have installed 208 an aqua-ozone hygienization system 100. In an exemplary embodiment, technician 302, by way of computing platform 732, can data communicate with server 732 or data communicate 206 with individual aqua-ozone hygienization system 100 to ascertain the operational status and location with a floor plan area 844.

Referring to FIG. 12, there is illustrated one example of a method of transitioning an aqua-ozone hygienization system 100 between a deodorizing atomized mist, a disinfection spray, and a purifying, deodorizing, and disinfecting immersion In an exemplary embodiment, the method begins in step 1002 by treating an item 202 with an atomized mist of the ozonated concentrate liquid 118, in a non-wetting deodorizing manner.

As better illustrated in at least FIGS. 3 and 4, the aqua-ozone hygienization system 100 comprises tank 104, and platform 142 is positioned inside tank 104. Platform 142 forms a water reservoir 140 located beneath platform 142. Platform 142 has a top surface for placing item 202 such as a towel, shirt, other clothing, or other suitable items to be treated. Electrochemical generator 516 can be configured to generate the ozonated concentrate liquid 118 from water 114. Circulating pump 128A can be configured 416 to draw water 114 from the water reservoir 140 and supply water 114 to the electrochemical generator 516. Nozzle 102 can be in fluid communication with the electrochemical generator 516. Nozzle 102 can be switchable 132 between dispensing the ozonated concentrate liquid 118 onto item 202 as the atomized mist or a spray. Egress port 162/130E can be configured to drain 136 the ozonated concentrate liquid 118 from the top surface of platform 142. In this regard, in an exemplary embodiment, platform 142 can form a liquid barrier and prevent mixing between the water reservoir 140 and ozonated concentrate liquid dispenses onto the top surface of platform 140.

The method continues in step 1004 by treating item 202 with a spray of the ozonated concentrate liquid in a wetting disinfecting manner. During treatments involving the atomized mist or the spray of the ozonated concentrate liquid 118 onto item 202, the egress port 162/130E can be configured to abate the accumulation of the ozonated concentrate liquid 118 on the top surface of the platform 142.

The method continues in step 1006 by treating item 202 with an immersion in a purifying, deodorizing, and disinfecting manner. During treatments involving immersion of item 202 in the ozonated concentrate liquid 118, nozzle 102 can be configured 132 as a spray, and the egress port 162/130E can be configured to allow the ozonated concentrate liquid 118 to accumulate on the top of platform 148 immersing item 202 in the ozonated concentrate liquid 118. Upon completion of the immersion, the egress port 162/130E can be configured to discharge 136 the ozonated concentrate liquid 118 from the top surface of platform 142.

Referring to FIG. 13, there is illustrated one example of a method of using the aqua-ozone hygienization system. In an exemplary embodiment, the method begins in step 1102 by transitioning, by user 304, the aqua-ozone hygienization system 100 between steps 1104, 1106, 1108, and 1110:

In step 1104 a deodorizing mist, wherein nozzle 102 can be configured to dispense the atomized mist onto the item that is placed on platform 142 in a non-wetting deodorizing manner.

In step 1106, a disinfecting spray, wherein nozzle 102 can be configured to dispense the spray onto the item that is placed on platform 142 in a wetting manner.

In step 1108, an immersion, wherein nozzle 102 can be configured for the spray and the ozonated concentrate liquid 118 accumulates on platform 142 immersing the item that is placed on platform 142 in the ozonated concentrate liquid 118 in a purifying, deodorizing, and disinfecting manner.

In step 1110, filling the external vessel 144 with the ozonated concentrate liquid 118, wherein the ozonated concentrate liquid 118 can be sprayed on items exterior to tank 104 and item 202 in a deodorizing and disinfecting manner.

Figure 14:
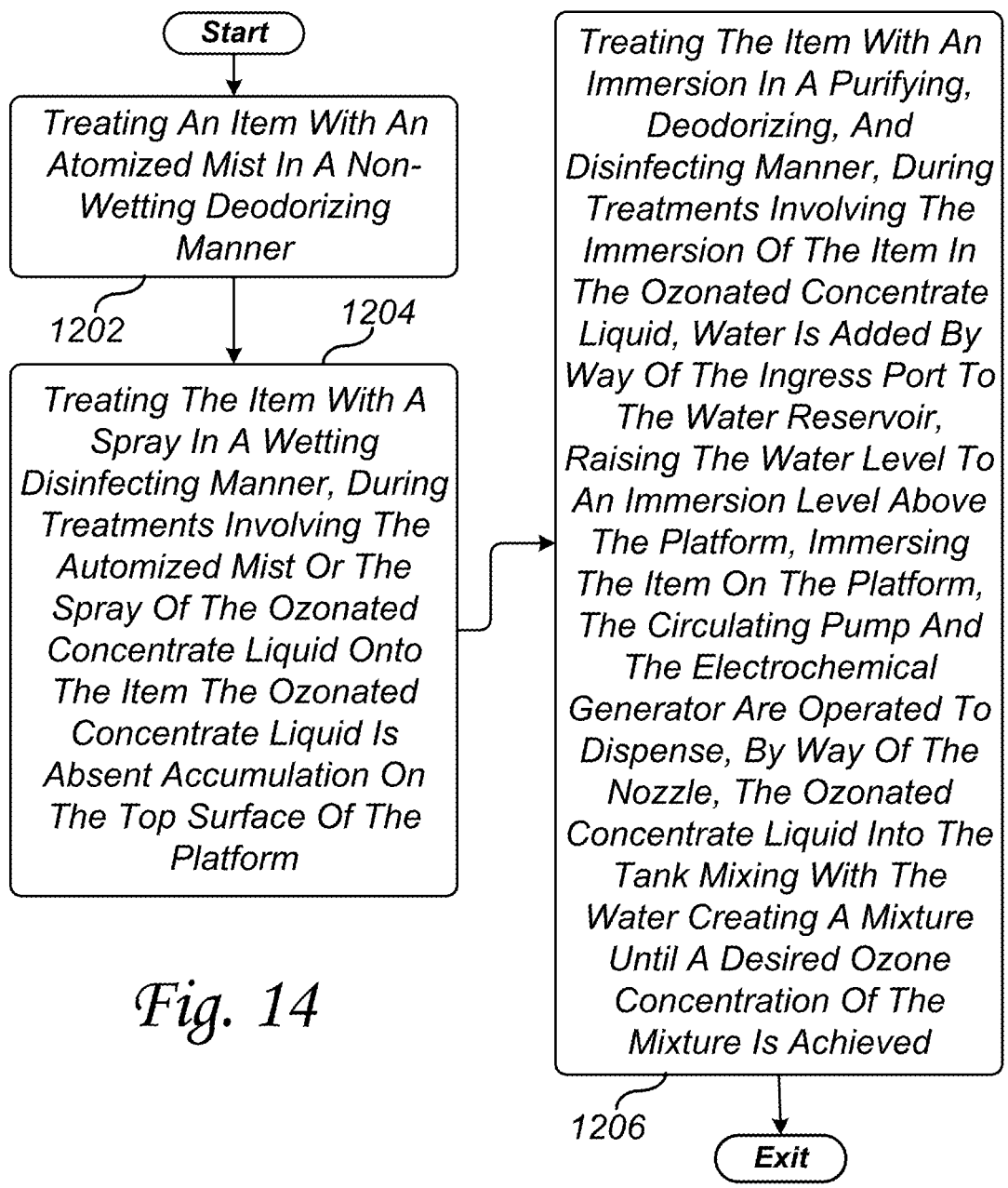

Referring to FIG. 14, there is illustrated one example of a method of transitioning an aqua-ozone hygienization system 100 between a deodorizing atomized mist, a disinfection spray, and a purifying, deodorizing, and disinfecting immersion. In an exemplary embodiment, the method begins in step 1202 by treating item 202 with an atomized mist of the ozonated concentrate liquid 118, in a non-wetting deodorizing manner.

As better illustrated in at least FIGS. 3 and 4, the aqua-ozone hygienization system 100 comprises tank 104, and platform 142 is positioned inside tank 104. Platform 142 forms a water reservoir 140 located beneath platform 142. Platform 142 has a top surface for placing item 202 such as a towel, shirt, other clothing, or other suitable items to be treated. Electrochemical generator 516 can be configured to generate the ozonated concentrate liquid 118 from water 114. Circulating pump 128A can be configured 416 to draw water 114 from the water reservoir 140 and supply water 114 to the electrochemical generator 516. Nozzle 102 can be in fluid communication with the electrochemical generator 516. Nozzle 102 can be switchable 132 between dispensing the ozonated concentrate liquid 118 onto item 202 as the atomized mist or a spray. Ingress port 164 can be configured to allow water 114 to fill the water reservoir 140.

The method continues in step 1204 by treating item 202 with a spray of the ozonated concentrate liquid in a wetting disinfecting manner. During treatments involving the atomized mist or the spray of the ozonated concentrate liquid 118 onto item 202, the egress port 162/130E can be configured to abate the accumulation of the ozonated concentrate liquid 118 on the top surface of the platform 142.

The method continues in step 1206 by treating item 202 with an immersion in a purifying, deodorizing, and disinfecting manner. During treatments involving immersion of item 202, water 114 can be added by way of the ingress port 164 to the water reservoir 140, raising the water level 410, permeating 152 platform 142, to an immersion level 412 above platform 142, immersing item 202 on platform 142. Circulating pump 128A and the electrochemical generator 516 are operated 416 to dispense, by way of the nozzle 102, the ozonated concentrate liquid 118 into tank 104 mixing with water 114 creating a mixture 114/118 until a desired ozone concentration 420 of mixture 114/118/422 is achieved. In this regard, in an exemplary embodiment, platform 142 can be permeable 152 allowing an overfilling of the water reservoir level 410 to rise through platform 142, allowing the water level to reach an immersion level 412.

Figure 15:
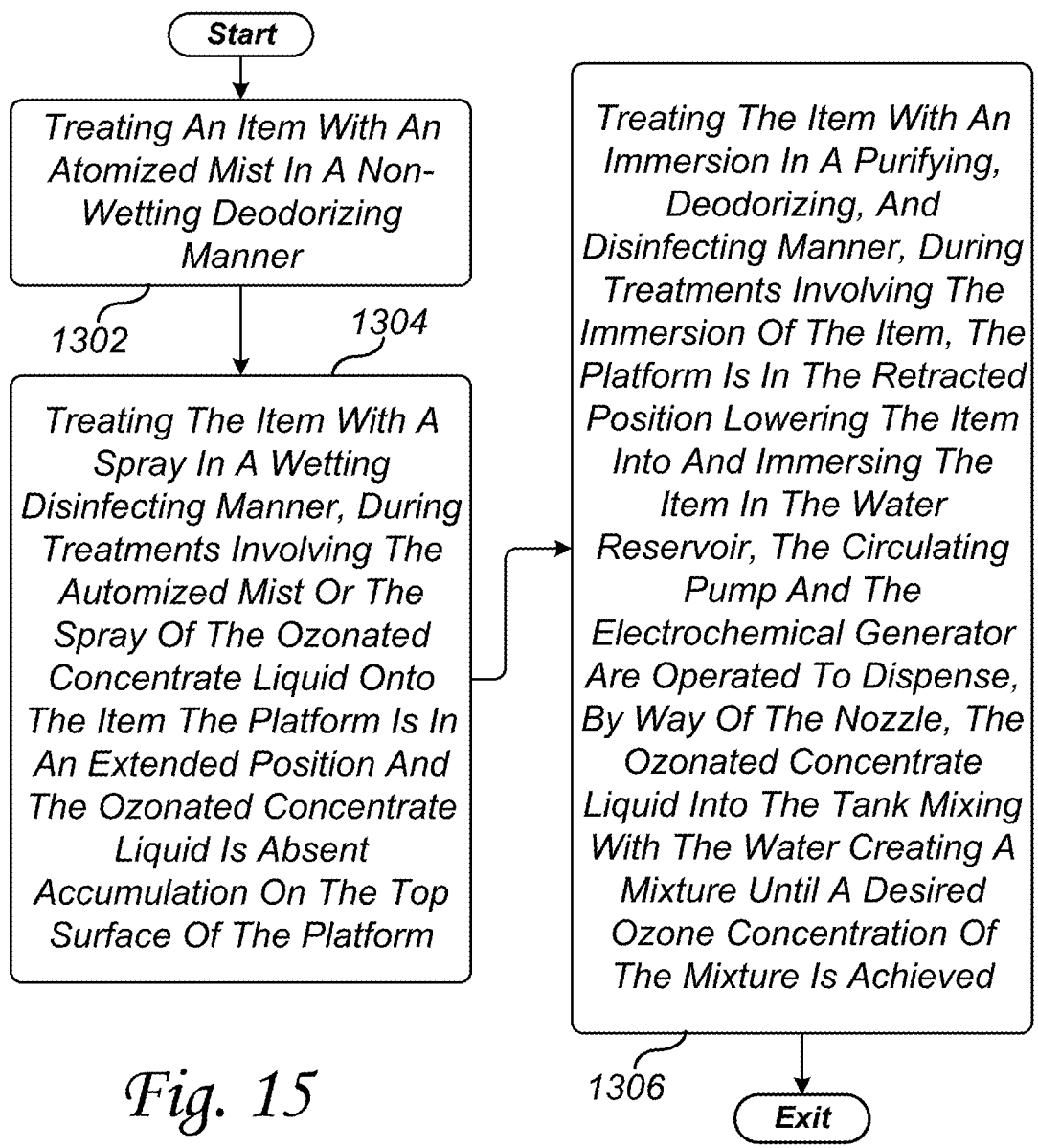

Referring to FIG. 15, there is illustrated one example of a method of transitioning an aqua-ozone hygienization system 100 between a deodorizing atomized mist, a disinfection spray, and a purifying, deodorizing, and disinfecting immersion In an exemplary embodiment, the method begins in step 1302 by treating an item 202 with an atomized mist of an ozonated concentrate liquid 118, in a non-wetting deodorizing manner.

As better illustrated in at least FIGS. 3 and 4, the aqua-ozone hygienization system 100 comprises tank 104, and platform 142 positioned within tank 104. Platform 142 in an extended position (better illustrated in at least FIG. 6 as platform 142A extended, motion 156A) forms a water reservoir 140 which comprises water located beneath platform 142 and in a retracted position (better illustrated in at least FIG. 6 as platform 142B retracted, motion 156B) platform 142 is immersed in the water 114 within the water reservoir 140. Platform 142 has a top surface for placing item 202 such as a towel, shirt, other clothing, or other suitable items to be treated. Electrochemical generator 516 can be configured to generate the ozonated concentrate liquid 118 from water 114. Circulating pump 128A can be configured 416 to draw water 114 from water reservoir 140 and supply water 114 to the electrochemical generator 516. Nozzle 102 can be in fluid communication with the electrochemical generator 516. Nozzle 102 can be switchable 132 between dispensing the ozonated concentrate liquid 118 onto item 202 as the atomized mist or a spray.

The method continues in step 1304 by treating item 202 with a spray of the ozonated concentrate liquid in a wetting disinfecting manner. During treatments involving the atomized mist or the spray of the ozonated concentrate liquid 118 onto item 202 platform 142 is in the extended position and the ozonated concentrate liquid 118 is absent accumulation on the top surface of the platform 142.

The method continues in step 1306 by treating item 202 with an immersion in a purifying, deodorizing, and disinfecting manner. During treatments involving the immersion of item 202, platform 142 can be in the retracted position lowering item 202 into and immersing item 202 in the water in the water reservoir 140. Circulating pump 128A and the electrochemical generator 516 are operated 416 to dispense, by way of nozzle 102, the ozonated concentrate liquid 118 into tank 104 mixing with the water 114 creating a mixture 114/118 until a desired ozone concentration 420 of mixture 114/118/422 is achieved.

Figure 16:
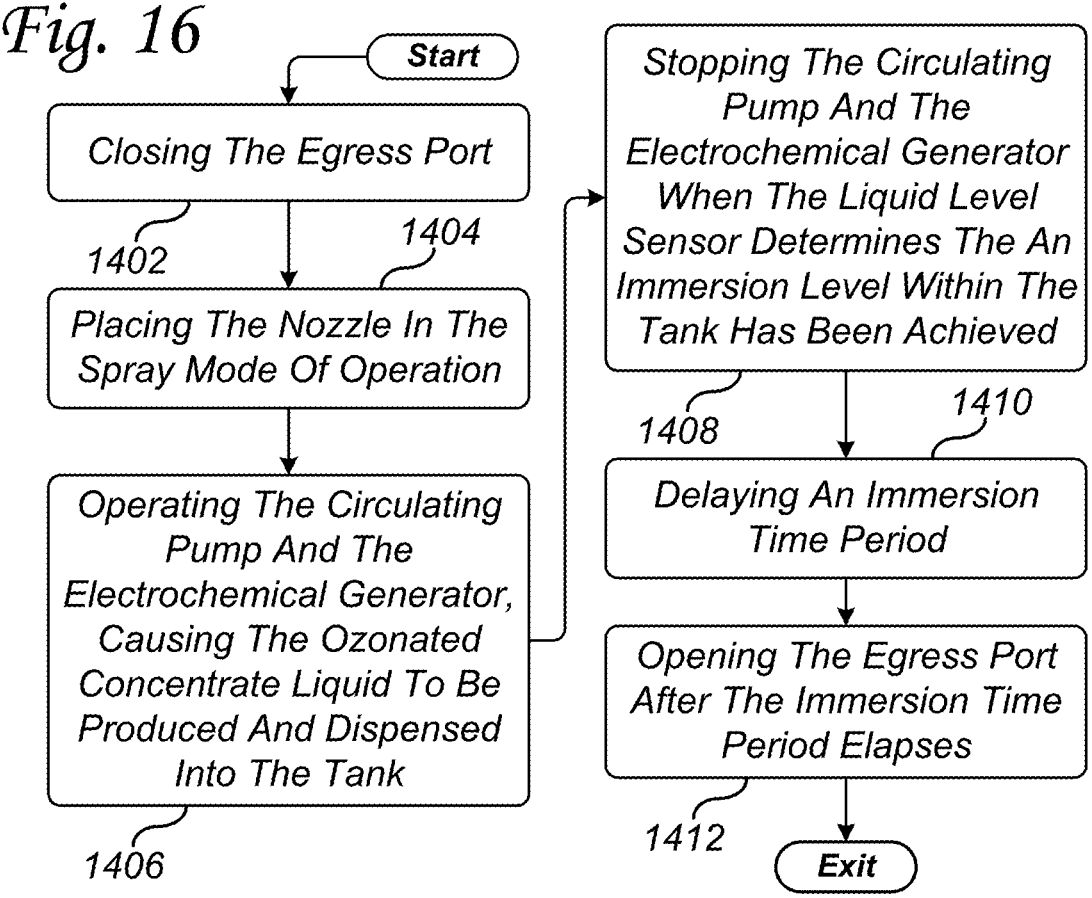
FIGS. 16-17 illustrate exemplary embodiments that can be used interchangeably with the methods of the present invention.

Referring to FIG. 16, there are illustrated exemplary embodiments that can be used interchangeably with the methods of the present invention. In an exemplary embodiment, the method begins in step 1402 by closing the egress port 162, then in step 1404 by placing the nozzle 102 in the spray mode 132 of operation.

The method continues in step 1406 by operating 416 (drawing water 114 from the water reservoir 140, producing ozonated concentrate liquid 118, and dispensing the ozonated concentrate liquid 118 into tank 104) the circulating pump 128B, and the electrochemical generator 516, causing the ozonated concentrate liquid 118 to be produced and dispensed into the tank 104.

The method continues in step 1408 by stopping 416 the circulating pump 128B and the electrochemical generator when the liquid level sensor 518 determines that an immersion level 412 within tank 104 of the ozonated concentrate liquid 118 has been achieved.

The method continues in step 1410 by delaying an immersion time period with item 202 immersed in the ozonated concentrate liquid 118. Such immersion time period can be in the range of 5 to 60 seconds, or other desired range as may be required and/or desired in a particular embodiment.

The method continues in step 1412 by opening the egress port 130E-F/162 after the immersion time period elapses, allowing the ozonated concentrate liquid 118 to be discharged 136 from tank 104. The method is then exited.

Figure 17:
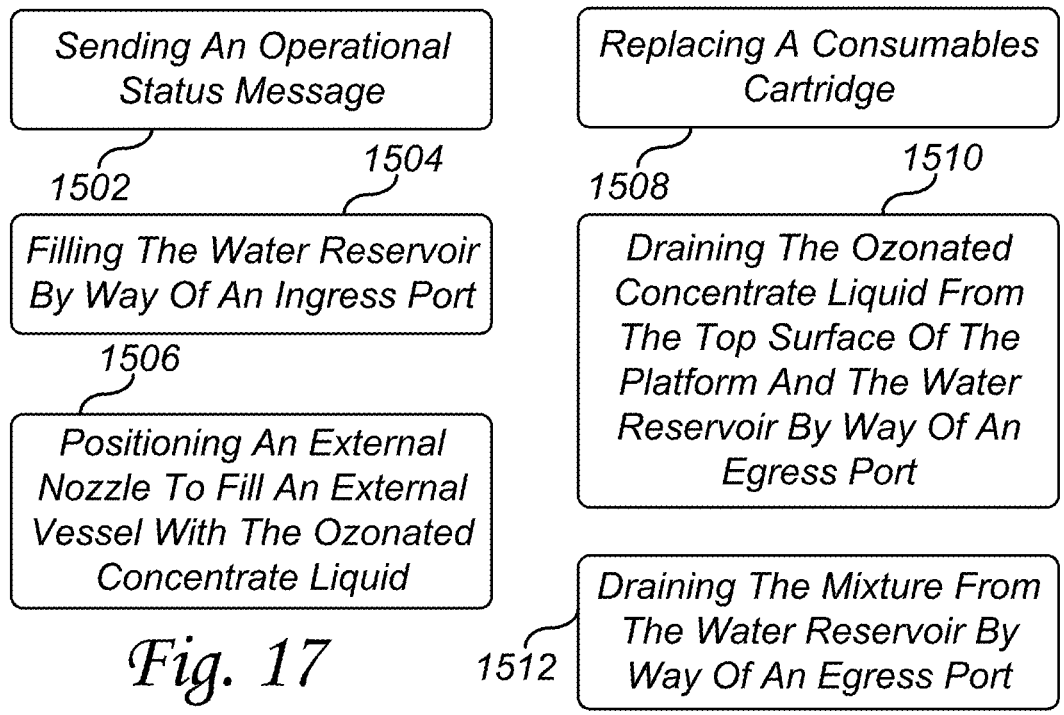

Referring to FIG. 17, there are illustrated exemplary embodiments that can be used interchangeably with the methods of the present invention.

In step 1502, sending an operational status message by way of a control system 500 to a remote data processing resource 702.

In an exemplary embodiment, the communication interface 508 can effectuate the actual data communication exchange with the remote data processing resource 702. In this regard, sending an operational status message by way of a communication interface 508 to a remote data processing resource 702. The control system comprises the communication interface 508. The control system can be integrated into the aqua-ozone hygienization system 100.

In an exemplary embodiment, in operation, the operational status message can be related to the operational performance of the electrochemical generator 516.

In an exemplary embodiment, in operation, the control system 500 can further comprise a global position system (GPS) 514. The operational status message can be related to the GPS location of the aqua-ozone hygienization system 100.

In a plurality of other exemplary embodiments, the operational status message can be related to other operational, performance, and other data or conditions as may be required and/or desired in a particular embodiment.

In step 1504, filling the water reservoir 140 by way of an ingress port 164. The aqua-ozone hygienization system 100 comprises the ingress port 164.

In step 1506, positioning an external nozzle, within a concave portion 120, to fill an external vessel 144 with the ozonated concentrate liquid 118. Tank 104 comprises the concave portion 120 along the exterior surface. The external vessel 144 fits and is storable, in a removable manner, within the concave portion 120.

In an exemplary embodiment, an external nozzle 122 can be positioned within a concave portion 120 and configured to fill an external vessel 144 with the ozonated concentrate liquid 118.

In step 1508, replacing a consumables cartridge 158 that is inserted, in a removable manner, into the aqua-ozone hygienization system 100. The consumables cartridge 158 comprises the electrochemical generator 516. In an exemplary embodiment, the consumables cartridge 158 can also comprise the ion exchange material 534, and other consumer items, as may be required and/or desired in a particular embodiment.

In step 1510, draining the ozonated concentrate liquid 118 from the top surface of the platform 142 and the water reservoir 140 by way of an egress port 162. The aqua-ozone hygienization system 100 comprises the egress port 162.

In step 1512, draining the mixture (of water 114 and ozonated concentrate liquid 118) from the water reservoir 140 by way of an egress port 162. The aqua-ozone hygienization system comprises the egress port 162.

The capabilities of the present invention can be implemented in software, firmware, hardware, or some combination thereof.

As one example, one or more aspects of the present invention can be included in an article of manufacture (e.g., one or more computer program products) having, for instance, computer-usable media. The media has embodied therein, for instance, computer-readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. An aqua-ozone hygienization system comprising:
a tank is configured to hold an item for hygienization, hygienization is effectuated by way of a user selecting between treating the item with an atomized mist in a non-wetting deodorizing manner, a spray in a wetting disinfecting manner, or an immersion in a purifying, deodorizing, and disinfecting manner;
a platform is positioned within the tank, the platform forms a water reservoir located beneath the platform, the platform having a top surface for placing the item to be treated;
an electrochemical generator is configured to generate an ozonated concentrate liquid from water;
a circulating pump is configured to draw water from the water reservoir and supply the water to the electrochemical generator;
a nozzle is in fluid communication with the electrochemical generator, the nozzle is switchable between dispensing the ozonated concentrate liquid onto the item as the atomized mist or as the spray; and
an egress port is configured to drain the ozonated concentrate liquid from the top surface of the platform;
wherein during treatments involving the atomized mist or the spray of the ozonated concentrate liquid onto the item the egress port is configured to abate accumulation of the ozonated concentrate liquid on the top surface of the platform; and
wherein during treatments involving the immersion of the item in the ozonated concentrate liquid the nozzle is configured as the spray and the egress port is configured to allow the ozonated concentrate liquid to accumulate on the top of the platform immersing the item in the ozonated concentrate liquid, upon completion of the immersion, the egress port is configured to discharge the ozonated concentrate liquid from the top surface of the platform.

2. The aqua-ozone hygienization system in accordance with claim 1, the electrochemical generator further comprises an ion exchange material.

3. The aqua-ozone hygienization system in accordance with claim 1, further comprising:
an ingress port is configured to allow water to fill the water reservoir.

4. The aqua-ozone hygienization system in accordance with claim 1, further comprising:
an ozone concentration sensor is configured to determine the ozone concentration level of the ozonate concentrate liquid.

5. The aqua-ozone hygienization system in accordance with claim 1, further comprising:
an external nozzle is positioned within a concave portion and configured to fill an external vessel with the ozonated concentrate liquid, the tank comprises the concave portion along the exterior surface, the external vessel fits and is storable, in a removable manner, within the concave portion.

6. The aqua-ozone hygienization system in accordance with claim 1, further comprising:
an external nozzle positioned external to the tank is configured to fill an external vessel.

7. The aqua-ozone hygienization system in accordance with claim 1, further comprising:
a consumables cartridge that is inserted, in a removable manner, into the aqua-ozone hygienization system, the consumables cartridge comprises the electrochemical generator.

8. A method of using the aqua-ozone hygienization system of claim 1, the method comprising the steps of:
transitioning, by the user, the aqua-ozone hygienization system between:
deodorizing mist, wherein the nozzle is configured to dispense the atomized mist onto the item that is placed on the platform in a non-wetting deodorizing manner;
disinfecting spray, wherein the nozzle is configured to dispense the spray onto the item that is placed on the platform in a wetting manner;
immersion, wherein the nozzle is configured for the spray and the ozonated concentrate liquid accumulates on the platform immersing the item that is placed on the platform in the ozonated concentrate liquid in a purifying, deodorizing, and disinfecting manner; and
filling the external vessel with the ozonated concentrate liquid, wherein the ozonated concentrate liquid is sprayed on items exterior to the tank in a deodorizing and disinfecting manner.

9. The aqua-ozone hygienization system in accordance with claim 1, further comprising:
a control system comprises a microcontroller, a memory, and a communication interface, the microcontroller is operationally related to the memory and the communication interface, the memory is encoded with instructions that when executed by the microcontroller perform the step of:
sending an operational status message by way of the communication interface control system to a remote data processing resource.

10. The aqua-ozone hygienization system in accordance with claim 1, wherein the operational status message is related to the operational performance of the electrochemical generator.

11. The aqua-ozone hygienization system in accordance with claim 1, the control system further comprises a global position system (GPS) that is operationally related to the microcontroller, wherein the operational status message is related to the GPS location of the aqua-ozone hygienization system.

12. The aqua-ozone hygienization system in accordance with claim 1, further comprising:
a control system comprises a microcontroller, a memory, and a liquid level sensor, the microcontroller is operationally related to the memory and the liquid level sensor, the memory is encoded with instructions that when executed by the microcontroller perform the steps of:
closing the egress port;
placing the nozzle in the spray mode of operation;
operating the circulating pump and the electrochemical generator, causing the ozonated concentrate liquid to be produced and dispensed into the tank;
stopping the circulating pump and the electrochemical generator when the liquid level sensor determines that an immersion level within the tank of the ozonated concentrate liquid has been achieved;
delaying an immersion time period with the item immersed in the ozonated concentrate liquid; and
opening the egress port after the immersion time period elapses, allowing the ozonated concentrate liquid to be discharged from the tank.

13. An aqua-ozone hygienization system comprising:
a tank is configured to hold an item for hygienization, hygienization is effectuated by way of a user selecting between treating the item with an atomized mist in a non-wetting deodorizing manner, a spray in a wetting disinfecting manner, or an immersion in a purifying, deodorizing, and disinfecting manner;
a platform is positioned within the tank, the platform forms a water reservoir located beneath the platform, the platform having a top surface for placing the item to be treated;
an electrochemical generator is configured to generate an ozonated concentrate liquid from water;
a circulating pump is configured to draw water from the water reservoir and supply the water to the electrochemical generator;
a nozzle is in fluid communication with the electrochemical generator, the nozzle is switchable between dispensing the ozonated concentrate liquid onto the item as the atomized mist or as the spray; and
an ingress port is configured to allow water to fill the water reservoir;
wherein during treatments involving the atomized mist or the spray of the ozonated concentrate liquid onto the item the ozonated concentrate liquid is absent accumulation on the top surface of the platform;
wherein during treatments involving the immersion of the item, water is added by way of the ingress port to the water reservoir, raising the water level to an immersion level above the platform, immersing the item on the platform, the circulating pump and the electrochemical generator are operated to produce and dispense, by way of the nozzle, the ozonated concentrate liquid into the tank mixing with the water creating a mixture until a desired ozone concentration of the mixture is achieved.

14. The aqua-ozone hygienization system in accordance with claim 13, further comprising:
an ozone concentration sensor is configured to determine the ozone concentration level of the mixture in the tank.

15. The aqua-ozone hygienization system in accordance with claim 13, further comprising:
an egress port is configured to drain the ozonated concentrate liquid from the top surface of the platform and the water reservoir.

16. The aqua-ozone hygienization system in accordance with claim 13, further comprising:
an external nozzle is positioned within a concave portion and configured to fill an external vessel with the ozonated concentrate liquid, the tank comprises the concave portion along the exterior surface, the external vessel fits and is storable, in a removable manner, within the concave portion.

17. A method of using the aqua-ozone hygienization system of claim 13, the method comprising the steps of:
transitioning, by the user, the aqua-ozone hygienization system between:
deodorizing mist, wherein the nozzle is configured to dispense the atomized mist onto the item that is placed on the platform in a non-wetting deodorizing manner;
disinfecting spray, wherein the nozzle is configured to dispense the spray onto the item that is placed on the platform in a wetting manner;
immersion, wherein the water level is increased in the tank, the ozonated concentrate liquid mixes with the water forming the mixture that immerses the item on the platform in a purifying, deodorizing, and disinfecting manner; and
filling the external vessel with the ozonated concentrate liquid, wherein the ozonated concentrate liquid is sprayed on items exterior to the tank in a deodorizing and disinfecting manner.

18. The aqua-ozone hygienization system in accordance with claim 13, further comprising:
a control system comprises a microcontroller, a memory, and a communication interface, the microcontroller is operationally related to the memory and the communication interface, the memory is encoded with instructions that when executed by the microcontroller perform the step of:
sending an operational status message by way of a control system to a remote data processing resource.

19. An aqua-ozone hygienization system comprising:
a tank is configured to hold an item for hygienization, hygienization is effectuated by way of a user selecting between treating the item with an atomized mist in a non-wetting deodorizing manner, a spray in a wetting disinfecting manner, or an immersion in a purifying, deodorizing, and disinfecting manner;
a platform is positioned within the tank, the platform in an extended position forms a water reservoir which comprises water located beneath the platform and in a retracted position is immersed into the water reservoir, the platform having a top surface for placing the item to be treated;
an electrochemical generator is configured to generate an ozonated concentrate liquid from water;
a circulating pump is configured to draw water from the water reservoir and supply the water to the electrochemical generator; and
a nozzle is in fluid communication with the electrochemical generator, the nozzle is switchable between dispensing the ozonated concentrate liquid onto the item as the atomized mist or as the spray;
wherein during treatments involving the atomized mist or the spray of the ozonated concentrate liquid onto the item the platform is in the extended position and the ozonated concentrate liquid is absent accumulation on the top surface of the platform;
wherein during treatments involving the immersion of the item, the platform is in the retracted position lowering the item into and immersing the item in the water reservoir, the circulating pump and the electrochemical generator are operated to produce and dispense, by way of the nozzle, the ozonated concentrate liquid into the tank mixing with the water creating a mixture until a desired ozone concentration of the mixture is achieved.

20. The aqua-ozone hygienization system in accordance with claim 19, further comprising:
an ozone concentration sensor is configured to determine the ozone concentration level of the mixture in the tank.

21. The aqua-ozone hygienization system in accordance with claim 19, further comprising:
an egress port is configured to drain the mixture from the water reservoir.

22. A method of using the aqua-ozone hygienization system of claim 19, the method comprising the steps of:
transitioning, by the user, the aqua-ozone hygienization system between:
deodorizing mist, wherein the platform is in the extended position, and the nozzle is configured to dispense the atomized mist onto the item that is placed on the platform in a non-wetting deodorizing manner;
disinfecting spray, wherein the platform is in the extended position, and the nozzle is configured to dispense the spray onto the item that is placed on the platform in a wetting manner;
immersion, wherein the platform is in the retracted position lowering the item into and immersing the item in the water reservoir, the circulating pump and the electrochemical generator are operated to dispense, by way of the nozzle, the ozonated concentrate liquid into the tank mixing with the water creating a mixture until a desired ozone concentration of the mixture is achieved; and
filling the external vessel with the ozonated concentrate liquid, wherein the ozonated concentrate liquid is sprayed on items exterior to the tank in a deodorizing and disinfecting manner.

* * * * *